(12) United States Patent
Bossard et al.

(10) Patent No.: US 7,714,114 B2
(45) Date of Patent: May 11, 2010

(54) CONJUGATES OF AN EPO MOIETY AND A POLYMER

(75) Inventors: Mary J. Bossard, Madison, AL (US); Gayle Stephenson, Madison, AL (US)

(73) Assignee: Nektar Therapeutics, San Carlos, CA (US)

(*) Notice: Subject to any disclaimer, the term of this patent is extended or adjusted under 35 U.S.C. 154(b) by 846 days.

(21) Appl. No.: 11/357,936

(22) Filed: Feb. 16, 2006

(65) Prior Publication Data
US 2006/0182711 A1 Aug. 17, 2006

Related U.S. Application Data

(60) Provisional application No. 60/653,451, filed on Feb. 16, 2005.

(51) Int. Cl.
*A61K 38/18* (2006.01)
(52) U.S. Cl. .................. 530/402; 424/78.38; 514/12
(58) Field of Classification Search ............... None
See application file for complete search history.

(56) References Cited

U.S. PATENT DOCUMENTS

| | | | |
|---|---|---|---|
| 4,904,584 A | 2/1990 | Shaw | |
| 5,106,954 A | 4/1992 | Fibi et al. | |
| 5,354,934 A | 10/1994 | Pitt et al. | |
| 5,476,653 A | 12/1995 | Pitt et al. | |
| 5,567,422 A | 10/1996 | Greenwald | |
| 5,621,080 A | 4/1997 | Lin | |
| 5,637,749 A | 6/1997 | Greenwald | |
| 5,756,349 A | 5/1998 | Lin | |
| 5,767,078 A | 6/1998 | Johnson et al. | |
| 6,077,939 A | 6/2000 | Wei et al. | |
| 6,340,742 B1 * | 1/2002 | Burg et al. | 530/351 |
| 6,583,272 B1 * | 6/2003 | Bailon | 530/397 |
| 6,586,398 B1 | 7/2003 | Kinstler et al. | |
| 6,753,165 B1 | 6/2004 | Cox et al. | |
| 2002/0002250 A1 | 1/2002 | Bentley et al. | |
| 2002/0081734 A1 | 6/2002 | Choi et al. | |
| 2002/0115833 A1 | 8/2002 | Burg et al. | |
| 2003/0191291 A1 | 10/2003 | Kochendoerfer et al. | |
| 2004/0082765 A1 | 4/2004 | Nakamura et al. | |
| 2004/0229318 A1 | 11/2004 | Heavner | |

FOREIGN PATENT DOCUMENTS

| | | |
|---|---|---|
| EP | 0605963 A2 | 7/1994 |
| EP | 0714402 B1 | 11/2000 |
| EP | 1 333 036 A1 | 8/2003 |
| WO | WO 90/12874 A2 | 11/1990 |
| WO | WO 91/05867 A1 | 5/1991 |
| WO | WO 93/25212 A1 | 12/1993 |
| WO | WO 94/04193 A1 | 3/1994 |
| WO | WO 96/40772 A2 | 12/1996 |
| WO | WO 96/40792 A1 | 12/1996 |
| WO | WO 97/16204 A1 | 5/1997 |
| WO | WO 98/05363 A2 | 2/1998 |
| WO | WO 99/03887 A1 | 1/1999 |
| WO | WO 99/52542 A1 | 10/1999 |
| WO | WO 00/32772 A2 | 6/2000 |
| WO | WO 00/42175 A1 | 7/2000 |
| WO | WO 01/02017 A2 | 1/2001 |
| WO | WO 01/76639 A2 | 10/2001 |
| WO | WO 01/91780 A1 | 12/2001 |
| WO | WO 02/19963 A2 | 3/2002 |
| WO | WO 02/49673 A2 | 6/2002 |
| WO | WO 2004/075923 A2 | 9/2004 |
| WO | WO 2005/000360 A2 | 1/2005 |

OTHER PUBLICATIONS

Enzon Pharmaceuticals Catalog, "Macromolecular Engineering Technologies," pp. 1-14 (2004).
Malik, et al., "Peg-Modified Erythropoietin with Improved Efficacy," *Exp Hematology* 28(7):106 (1995) *Abstract only*.
Monkarsh, et al., "Positional Isomers of Monopegylated Interferon Alpha-2a:Isolation, Characterization, and Biological Activity," Analytical Biochemistry, Academic Press, San Diego, CA, US, 247(2):434-440 (1997).
Nektar Advanced PEGylation Catalog, "Polyethylene Glycol and Derivatives for Advanced PEGylation," pp. 1-21 (2003).
Nektar Advanced PEGylation Catalog, "Polyethylene Glycol and Derivatives for Advanced PEGylation," pp. 1-24 (2004).
Nektar Advanced PEGylation Catalog, "Polyethylene Glycol and Derivatives for Advanced PEGylation," pp. 1-30 (2005-2006).
NOF Corporation Catalog, "Peg Derivatives, Phospholipid and Drug Delivery Materials for Pharmaceuticals," 1: 2-46 (2003).
NOF Corporation Catalog, "Peg Derivatives, Phospholipid and Drug Delivery Materials for Pharmaceuticals," 2: 2-50 (2003).
Polypure Products Catalog, Apr. 2004.
Polypure Products Catalog, Apr. 2005.
Quanta Biodesign Catalog, "Labeling, Derivatization and Crosslinking Reagents for Biological and Related Materials with dPEG," pp. 1-38, Mar. 12, 2004.
Quanta Biodesign Catalog, "Labeling, Derivatization and Crosslinking Reagents for Biological and Related Materials with dPEG," pp. 1-31, Nov. 5, 2004.
Quanta Biodesign Product Catalog, "Leading Innovator, Producer and Provider of Monodisperse Discrete PEG (dPEG) Derivatives," pp. 1-51, Jul. 18, 2005.
Quanta Biodesign Product Catalog, "Leading Innovator, Producer and Provider of Monodisperse Discrete PEG (dPEG) Derivatives," pp. 1-51, Nov. 11, 2005.
Shearwater Corporation Catalog, "Polyethylene Glycol and Derivatives for Biomedical Applications," pp. 1-17 (2001).

(Continued)

*Primary Examiner*—Christopher R. Tate
*Assistant Examiner*—Roy Teller
(74) *Attorney, Agent, or Firm*—Naishadh N. Desai; Mark A. Wilson; Susan T. Evans

(57) ABSTRACT

Conjugates of an EPO moiety and one or more non-peptidic water-soluble polymers are provided. Typically, the non-peptidic water-soluble polymer is poly(ethylene glycol) or a derivative thereof. Also provided are compositions comprising such conjugates, methods of making conjugates, and methods of administering compositions comprising such conjugates to a patient.

24 Claims, 3 Drawing Sheets

OTHER PUBLICATIONS

Shearwater Polymers, Inc., Catalog, "Functionalized Biocompatible Polymers for Research and Pharmaceuticals: Polyethylene Glycol and Derivatives," pp. 2-50 (2000).

Shearwater Polymers, Inc., Catalog, "Polyethylene Glycol and Derivatives," pp. 2-53 (1997-1998).

Shearwater Polymers, Inc., Catalog, pp. 2-49 (1995).

Boissel, J.P. et al., "Erythropoietin structure-function relationships. Mutant proteins that test a model of tertiary structure", *The Journal of Biological Chemistry*, 268(21):15983-15993 (1993).

Cheetham, J.C. et al., "NMR structure of human erythropoietin and a comparison with its receptor bound conformation", *Nature Structural Biology*, 5(10):861-866 (1998).

The International Search Report and Written Opinion for PCT application PCT/US2006/005850, search report dated Apr. 24, 2007, 11 pages (2007).

Elliott, S. et al., "Mapping of the active site of recombinant human erythropoietin", *Blood.*, 89(2):493-502 (1997).

Mathews, D.J. et al., "A sequential dimerization mechanism for erythropoietin receptor activation", *Proc. Natl. Acad. Sci. U.S.A.*, 93:9471-9476 (1996).

Syed, R.S. et al., "Efficiency of signalling through cytokine receptors depends critically on receptor orientation", *Nature*, 395:511-516 (1998).

* cited by examiner

SEQUENCE LISTING

<160> NUMBER OF SEQ ID NOS: 4

<210> SEQ ID NO 1
<211> LENGTH: 165

```
<212> TYPE: PRT
<213> ORGANISM: Homo sapiens

<400> SEQUENCE: 1

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp
                165

<210> SEQ ID NO 2
<211> LENGTH: 166
<212> TYPE: PRT
<213> ORGANISM: Homo sapiens

<400> SEQUENCE: 2

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165
```

```
<210> SEQ ID NO 3
<211> LENGTH: 7
<212> TYPE: PRT
<213> ORGANISM: Homo sapiens

<400> SEQUENCE: 3

Val Asn Phe Tyr Ala Trp Lys
 1               5

<210> SEQ ID NO 4
<211> LENGTH: 8
<212> TYPE: PRT
<213> ORGANISM: Homo sapiens

<400> SEQUENCE: 4

Val Asn Phe Tyr Ala Trp Lys Arg
 1               5
```

CONJUGATES OF AN EPO MOIETY AND A POLYMER

CROSS REFERENCE TO RELATED APPLICATIONS

This application claims the benefit of priority to Provisional Patent Application No. 60/653,451, filed Feb. 16, 2005, the contents of which are hereby incorporated herein by reference.

FIELD OF THE INVENTION

Among other things, one or more embodiments of the present invention relate generally to conjugates comprising an EPO moiety (i.e., a moiety having erythropoietin activity) and a polymer. In addition, the invention relates to (among other things) compositions comprising conjugates, methods for synthesizing conjugates, and methods for treating patients by administering such conjugates.

BACKGROUND OF THE INVENTION

One important function of the human hematopoietic system is erythropoiesis, which is the production of red blood cells or "erythrocytes." Erythropoiesis is vitally important as it is the process whereby new red blood cells are generated as old red blood cells degenerate. In this way, a continuous supply of red blood cells is ensured, thereby guaranteeing the continuous oxygenation of biological tissues.

In humans, erythropoiesis occurs in the presence of a protein hormone called "erythropoietin" abbreviated as "EPO" which serves to stimulate the division and differentiation of progenitor cells located in bone marrow. Over a period of about four days, progenitor cells mature into red blood cells and are released into the general circulation. A typical red blood cell lives for about four months in the systemic circulation. Typically, control of the erythropoietic cycle is governed by a negative feedback mechanism whereby the increased oxygenation of the tissues caused by increased numbers of red blood cells results in a decrease in the production of erythropoietin.

Naturally-occurring EPO is a glycoprotein hormone with 165 amino acids, 4 glycosylation sites on amino-acid positions 24, 38, 83, and 126, and a molecular weight of about 34,000. EPO is produced in vivo as a precursor protein with a signal peptide of 23 amino acids and can occur in three forms. The DNA sequences encoding EPO have been reported. See, for example, U.S. Pat. No. 4,703,008.

Pharmacologically, EPO has been administered to humans for the treatment of a variety of conditions, including the treatment of patients suffering from anemia. Specifically, for example, EPO is indicated for (a) anemia associated with chronic renal failure, (b) anemia related to zidovudine therapy in HIV-infected patients, and (c) anemia in cancer patients undergoing chemotherapy. In addition, EPO has been used to reduce allgeneic blood transfusion in patients undergoing surgery, and for pruritus associated with renal failure.

One drawback associated with current forms of EPO therapy is the frequency of dosing. Because EPO therapy typically requires daily injections, patients dislike the inconvenience and discomfort associated with this regimen.

One proposed solution to these problems has been to provide a prolonged release form of EPO. For example, U.S. Pat. No. 5,416,071 describes a water-soluble composition comprising EPO, hyaluronic acid, and human serum albumin. Such compositions, however, may not provide sufficient activity over the desired period of time.

Others have suggested the use of PEGylation technology, or the attachment of a poly(ethylene glycol) derivative to a protein such as EPO, in order to prolong EPO's in vivo half-life. For example, U.S. Patent Application Publication No. 2004/0082765 describes conjugation of PEG derivatives bearing a succinimidyl lower fatty acid ester (such as a PEG derivative bearing succinimidyl propionate or succinimidyl butyrate moiety).

U.S. Patent Application Publication No. 2002/0081734 describes preparing a mutein of EPO having a cysteine residue introduced at the thirty-eighth position and then PEGylating the mutein at the introduced cysteine residue via a PEG-maleimide derivative. No specific structure of the PEG-maleimide derivative was described in the publication.

U.S. Pat. No. 6,753,165 describes methods for making soluble proteins (including EPO) having free cysteines. The publication also describes modifying the soluble proteins by attaching a PEG moiety at the free cysteine via a PEG derivative bearing a vinylsulfone, maleimide or iodacetyl moiety. With respect to attaching the PEG, the publication describes the necessity for performing a partial reduction step in order to increase the relatively unreactive free cysteine on the protein. International Patent Publication WO 90/12874 also describes cysteine-added variants of EPO, wherein a PEG is attached to the added cysteine residue.

International Patent Publication WO 01/76639 describes myelopoietin conjugates, which refers to a fusion protein prepared from a modified human IL-3 polypeptide sequence linked to another molecule such as EPO.

U.S. Pat. No. 6,077,939 describes a process for attaching a PEG to the N-terminal alpha carbon of a protein (such as EPO) that has previously been subjected to a transamination reaction. The described conjugates can contain a PEG linked to EPO via a hydrazone, reduced hydrazone, oxime, or reduced oxime linkage.

U.S. Pat. No. 6,340,742 describes PEG-EPO conjugates wherein EPO is modified by the addition of from 1 to 6 glycosylation sites and covalently linked to from one to three lower alkoxy poly(ethylene glycol) groups, each poly(ethylene glycol) group attached via a specific linkage. The described conjugates are prepared by first "activitating" the EPO by covalently linking one or more protected thiol groups to EPO, followed by removal of the group protecting the thiol. Once the protecting group is removed, the step of attaching certain reagents at the unprotected thiol is performed.

U.S. Patent Application Publication No. 2003/0191291 describes proteins having EPO activity that are prepared using non-recombinant technology. The publication further describes such proteins that are polymer-modified in a defined manner.

U.S. Patent Application Publication No. 2002/0115833 describes an EPO glycoprotein covalently linked to one poly(ethylene glycol) group by way of a specific linkage containing an amide bond with the N-terminal alpha-amino group of the EPO glycoprotein.

EP 0 714 402 describes conjugates of polymers with proteins such as EPO. The poly(ethylene glycol) polymers used to form the conjugates have molecular weights of up to about 10,000.

International Patent Publication WO 96/40792 describes conjugates prepared from a polymer comprising the following structure: $\text{Poly}(-O-C=O-Y)_m$, wherein Y is a halogen or nitrile, m is an integer from 1 to 25, and Poly defines a synthetic or a naturally occurring polymer.

Notwithstanding these described conjugates, however, there remains a need to provide conjugates or compositions of EPO that satisfy one or more of the following: conjugates formed from different PEG derivatives (e.g., PEGs having different structures, reactive groups, and so forth); conjugates formed from PEG derivatives having different weight average molecular weights (e.g., greater than about 10,000); conjugates wherein the polymer is not attached primarily at lysine position 52; conjugates formed from recombinant EPO rather than muteins or fusion proteins thereof; compositions that are substantially homogeneous in terms of their EPO-PEGmer content (e.g., monoPEGylated EPO, diPEGylated EPO, etc.), compositions that are well-defined and reproducible in terms of EPO-PEGmer content and positional isoforms thereof, and conjugates that can be formed in relatively few steps and without the need to carry out partial reduction steps or other synthetic transformations (e.g., transamination reactions, addition of thiol groups, and so forth). Ideally, such a conjugate will possess suitable bioactivity in vivo, and possess a circulating half-life such that blood or plasma levels of EPO are sustained over a longer period of time in comparison to currently marketed formulations—such that a pharmaceutical preparation comprising such a conjugate can be administered less frequently than the currently marketed formulations, thereby providing a distinct advantage over currently available EPO formulations.

Thus, there remains a need in the art to provide additional, beneficial conjugates of water-soluble polymers and moieties having EPO activity. Among other things, one or more embodiments of the present invention is therefore directed to such conjugates as well as to compositions comprising the conjugates and related methods as described herein, which are believed to be new and completely unsuggested by the art.

SUMMARY OF THE INVENTION

Accordingly, a conjugate is provided, the conjugate comprising an EPO moiety covalently attached, either directly or through a spacer moiety, to a non-peptidic water-soluble polymer. The conjugate is typically provided as part of a composition comprising a plurality of conjugates, where such plurality of conjugates may include conjugates having different numbers of water-soluble polymers attached thereto (e.g., an EPO monomer having one water-soluble polymer attached thereto, an EPO dimer having two water-soluble polymers attached thereto, and so on), and/or conjugates which differ in the site or sites of attachment of the water-soluble polymer to EPO.

In one or more embodiments of the invention a composition is provided, the composition comprising a plurality of conjugates, each conjugate in the plurality comprised of human EPO attached, either directly or through a spacer moiety, to a non-peptidic water-soluble polymer, wherein the composition is not a pure composition of a single positional isoform such as monoPEGylated EPO. That is, the composition comprises a mixture of monoPEGylated EPO positional isoforms, preferably although not necessarily, wherein the composition comprises (a) less than 50% of monoPEGylated EPO at the lysine residue at position 52, (b) less than 50% of monoPEGylated EPO at the N-terminal amine, or (c) both.

In one or more embodiments of the invention a composition is provided, the composition comprising a plurality of conjugates, each conjugate in the plurality comprised of human EPO attached, either directly or through a spacer moiety, to a non-peptidic water-soluble polymer, wherein the composition contains less than 50% of the conjugates having the non-peptidic water-soluble polymer attached to the lysine residue at position 52 of the native human EPO.

In one or more embodiments of the invention a conjugate is provided, the conjugate comprised of an EPO moiety covalently attached, either directly or through a spacer moiety, to a non-peptidic water-soluble polymer, wherein the non-peptidic water-soluble polymer has a branched structure, a forked structure, or both.

In one or more embodiments of the invention a conjugate is provided, the conjugate comprising an EPO moiety covalently attached to a non-peptidic water-soluble polymer via an amide linkage. The amide linkage is part of a spacer moiety having an organic radical substituent (e.g., an alkyl group) at the carbon atom alpha ($\alpha$) to the carbonyl group of the amide linkage.

According to one or more particular embodiments of the invention, a conjugate of EPO comprises the structure:

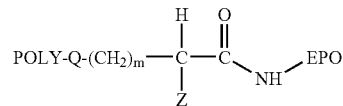

where POLY is a polyalkylene oxide, Q is an optional linking group having a length of from one to 10 atoms, m is an integer ranging from 0 to 20, Z is selected from the group consisting of alkyl, substituted alkyl, aryl and substituted aryl, EPO is a residue of erythropoietin, and "—NH-EPO" represents an amino group of EPO.

Preferably, POLY is a polyethylene glycol, and may possess any of a number of architectures, e.g., linear, branched, and/or forked.

Typically, POLY possesses a weight average molecular weight falling within one of the following ranges: from about 10,000 Daltons to about 100,000 Daltons, from about 10,000 Daltons to about 60,000 Daltons, from about 15,000 Daltons to about 50,000 Daltons, and from about 20,000 Daltons to about 45,000 Daltons. In one or more particular embodiments, POLY is a PEG possessing a weight average molecular weight selected from the group consisting of about 20 kilodaltons, about 30 kilodaltons, about 40 kilodaltons, and about 50 kilodaltons. In one particularly preferred embodiment, POLY is a PEG having a weight average molecular weight that is about 30 kilodaltons. In yet one or more particular embodiments, POLY is a PEG comprising an end-capping group such as methyl, ethyl, benzyl, and the like.

In reference to the structure above, Q is an optional linking group, meaning that the group may or may not be present. In one or more embodiments of the invention, Q is absent. In yet one or more additional embodiments, Q is present and possesses a length ranging from one to ten atoms, preferably from one to seven atoms, or even more preferably from one to five atoms, and may contain a heteroatom such as O, N, or S.

In reference to the structure above, m is an integer referring to the number of methylene subunits in the spacer moiety interposed between POLY and —NH-EPO. In one or more embodiments, the integer m is selected from the group consisting of 0, 1, 2, 3, 4, 5, 6, 7, 8, 9, and 10. Preferably, m is an integer ranging from 1 to 6, or more preferably from 1 to 5. In one or more embodiments, m is 1, 2 or 3.

In reference to the structure above, Z refers to a substituent on the carbon alpha to the carbonyl group. In one or more embodiments, Z is lower alkyl or substituted lower alkyl, e.g., methyl, ethyl, n-propyl, isopropyl, n-butyl, or isobutyl. Preferably, Z is methyl.

In one or more embodiments, a conjugate of the invention comprises the structure:

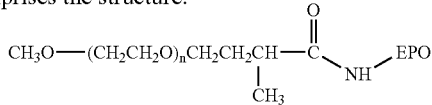

where n ranges from about 200 to about 1400. In one or more additional embodiments, n ranges from about 300 to about 1150, or from about 400 to about 900.

In one or more embodiments, EPO corresponds to human EPO, e.g., SEQ ID NO:1 or SEQ ID NO:2.

In yet one or more additional embodiments, an EPO conjugate of the invention (such as that described by the preceding structures) is a monoPEGylated EPO conjugate, that is to say, EPO having only one non-peptidic and water-soluble polymer such as PEG covalently attached to EPO. Also provided herein is a diPEGylated EPO conjugate, where EPO is covalently attached to only two water-soluble polymers such as PEG. The polymer may be attached to any reactive amine site on EPO, such as one or more of the following: lysine 20, 45, 52, 97, 116, 140, 153, 155, or the N-terminus. Also provided is a composition comprising both monoPEGylated EPO and diPEGylated EPO, e.g., corresponding to one or more of the structures provided herein.

Also provided herein are compositions comprising a plurality of EPO conjugates. In one or more particular embodiments, a composition of the invention is one wherein about greater than 85%, or even 90% of the PEG-EPO conjugates in the composition are monoPEGylated. In one more particular embodiments, provided is a composition of monoPEGylated EPO conjugates, wherein a minority (e.g., less than 50%) of the monoPEGylated EPO conjugate species in the composition possess polymer, e.g., PEG, covalently attached at lysine 52.

In yet one or more particular embodiments, and in particular those described by the above structures, provided is a composition of monoPEGylated EPO conjugates, wherein a minority (e.g., less than 50%) of the monoPEGylated EPO conjugate species in the composition possess a polymer, e.g., PEG, covalently attached at the N-terminus. In a preferred embodiment, provided is a composition of monoPEGylated EPO conjugates, wherein (i) less than 50% of the monoPEGylated species in the composition possess a polymer, e.g., PEG, covalently attached to lysine 52, and (ii) less than 50% of the monoPEGylated species in the composition possess a polymer, e.g., PEG, covalently attached at the N-terminus.

Also provided in one or more embodiments of the invention are EPO conjugates corresponding to one or more of the following structures:

where n corresponds to the values previously described.

Also provided is an EPO conjugate corresponding to any one or more of the structures provided herein, e.g., in Tables 1, 2 or 3.

In one or more embodiments of the invention, the EPO conjugate is bioactive in vivo, and possesses a bioactivity that is at least about 5%, or 10%, or 15%, or 20%, or 30%, or 40% or 50% or 60% or 70% or 80% or 90% or greater that of the unmodified EPO moiety itself.

In one or more embodiments of the invention, the EPO conjugate, when administered in vivo, demonstrates a pharmacokinetic profile that is improved over that of either unmodified EPO or currently marketed EPO-moieties such as Aranesp® erythropoietin.

In yet another aspect, the invention is directed, in one or more embodiments, to a method for preparing an EPO conjugate as described herein. Such method comprises the step of contacting one or more polymeric reagents with an EPO moiety under conditions sufficient to result in a conjugate comprising an EPO moiety covalently attached, either directly or through a spacer moiety comprised of one or more atoms, to a water-soluble polymer, wherein the method for preparing the conjugate lacks a partial reduction step.

In yet another aspect, the invention is directed, in one or more embodiments, to a method for preparing a conjugate comprising the step of contacting one or more polymeric reagents with an EPO moiety under conditions sufficient to result in a conjugate comprising an EPO moiety covalently attached, either directly or through a spacer moiety comprised of one or more atoms, to a water-soluble polymer, wherein the method for preparing the conjugate lacks a reduction step.

In yet another aspect, the invention is directed, in one or more embodiments, to a method for preparing a conjugate comprising the step of contacting one or more polymeric reagents to an EPO moiety under conditions sufficient to result in a conjugate comprising an EPO moiety covalently attached, either directly or through a spacer moiety comprised of one or more atoms, to a water-soluble polymer, wherein the method lacks a transaminiation step.

In yet another aspect, the invention is directed, in one or more embodiments, to a method for preparing a conjugate comprising the step of contacting one or more polymeric reagents to an EPO moiety under conditions sufficient to result in a conjugate comprising an EPO moiety covalently attached, either directly or through a spacer moiety comprised of one or more atoms, to a water-soluble polymer, wherein the method lacks a step requiring the introduction of a thiol group into the EPO moiety, or where the the EPO moiety itself is not an EPO-cysteine mutein.

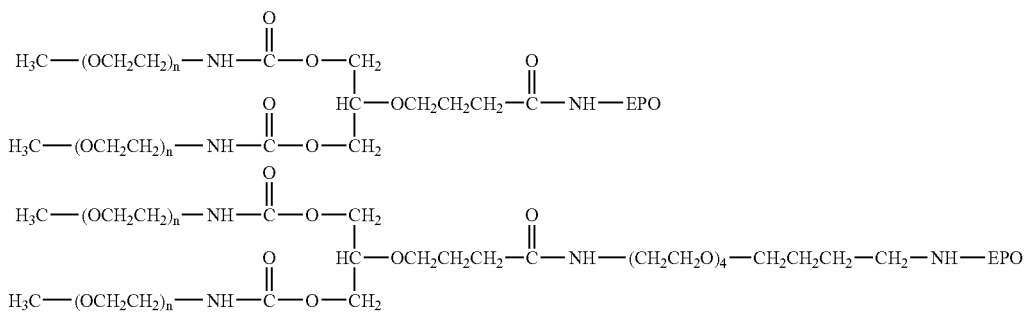

In yet another aspect, the invention provides a method for preparing a conjugate of EPO, whereby the method is effective to provide a composition comprising a plurality of polyalkylene oxide conjugates of EPO wherein a minority of the conjugate species formed possess a polyalkylene oxide covalently attached at lysine 52. The method comprises the steps of: (i) protecting reactive amino groups on an EPO moiety with a cyclic dicarboxylic acid anhydride protecting reagent to form an amino-protected EPO moiety, (ii) reacting a polyalkylene oxide reagent comprising a leaving group X with the amino-protected EPO moiety under conditions effective to promote reaction of one or more unprotected amino sites on EPO with the polyalkylene oxide reagent, to thereby form a polyalkylene oxide-amino protected-EPO conjugate, and (iii) deprotecting the polyalkylene oxide-amino protected-EPO conjugate to provide a composition comprising a plurality of polyalkylene oxide EPO conjugates wherein a minority of the conjugate species possess a polyalkylene oxide covalently attached at lysine 52.

In yet another aspect, the invention is directed to a method for preparing a conjugate of EPO, where the method includes the steps of:

reacting a polymer comprising the structure:

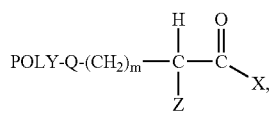

where the variables are as previously described, and X is a leaving group (e.g., chlorine, bromine, N-succinimidyloxy, sulfo-N-succinimidyloxy, 1-benzotriazolyloxy, hydroxyl, 1-imidazolyl, p-nitrophenyloxy, etc.,), with erythropoietin (EPO), under conditions effective to promote reaction of one or more amino sites on EPO with the polymer, to thereby form a biologically active conjugate comprising the structure:

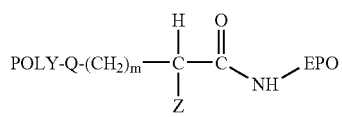

where the variables are as previously described.

In one or more embodiments of a method of preparing a polymer-EPO conjugate, the reacting step further comprises combining an aqueous solution of the polymer reagent with an aqueous solution of EPO to form a polymer-EPO reaction mixture. The pH of the polymer-EPO reaction mixture is typically in a range or is adjusted to be in a range from about 5 to about 8.5, preferably from about 5 to 8, and more preferably from about 5.5 to 7.5.

In yet one or more embodiments of a method for preparing a polymer-EPO conjugate, the polymer reagent is combined at a 5-fold or greater molar excess relative to EPO, preferably at a 10-fold or greater molar excess relative to EPO, and even more preferably at a 20-fold or greater molar excess relative to EPO.

In one or more additional embodiments of a method of preparing a polymer-EPO conjugate, the reacting step further comprises, after combining, stirring the reaction mixture for about 1-24 hours at a temperature ranging from about −10° C. to about 40° C. In yet one or more additional embodiments, stirring is carried out at ambient (e.g., room) temperature.

In yet one or more additional embodiments of a method for preparing a polymer-EPO conjugate, the method comprises, prior to the reacting step, protecting the amino groups of EPO (typically those that are most reactive) with a cyclic dicarboxylic acid anhydride protecting agent, e.g., a maleic or citraconylic anhydride, to form an amino-protected EPO. Preferably, the protecting agent is dimethylmaleic anhydride.

In yet one or more additional embodiments of a method for preparing a polymer-EPO conjugate, the method further comprises, after the reacting step, deprotecting the amino groups of the amino-protected EPO. In one or more embodiments, such method is effective to form a conjugate of EPO wherein a minority of the conjugate species have a polyalkylene oxide covalently attached at lysine 52, and optionally, and/or a minority of the conjugate species have a polyalkylene oxide covalently attached at the N-terminus.

One or more embodiments of a method for preparing a polymer-EPO conjugate further comprise, after the reacting step, purifying the resulting conjugate(s).

In one or more embodiments of such method, the polymer reagent comprises the structure:

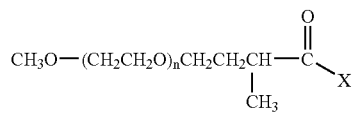

wherein X is a leaving group and n is an integer from about 200 to about 1400, and the conjugate comprises the structure:

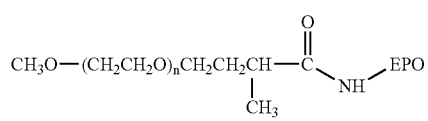

where EPO is a residue of erythropoietin and n is an integer from about 200 to about 1400.

In yet one or more embodiments of the above-described method(s), the polymer reagent comprises the structure:

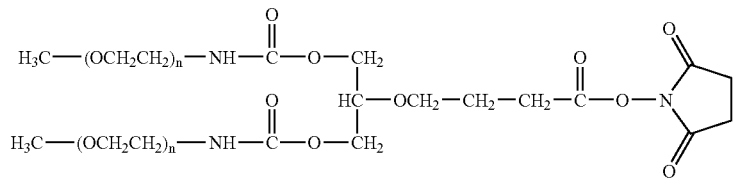

wherein each n is an integer from about 200 to about 1400, and the conjugate comprises the structure:

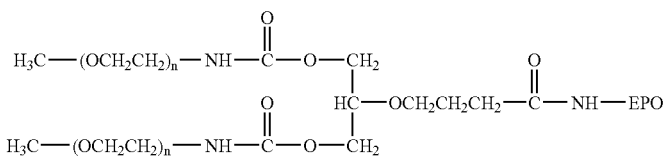

wherein EPO is a residue of erythropoietin and each n is an integer from about 200 to about 1400.

In yet one or more embodiments of the above-described method(s), the polymer reagent comprises the structure:

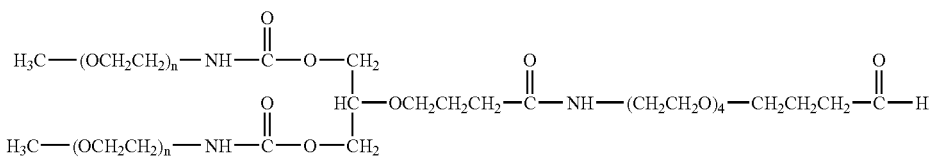

wherein each n is an integer from about 200 to about 1400, and the conjugate comprises the structure:

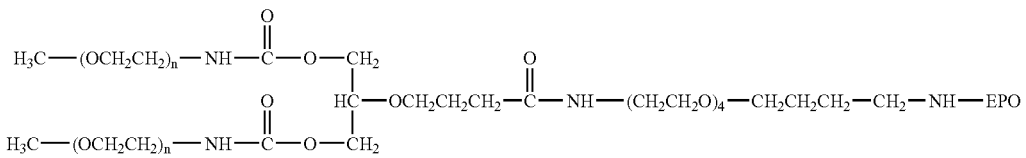

wherein each n is an integer from about 200 to about 1400 and EPO is a residue of erythropoietin.

In one or more embodiments of the invention a composition is provided, the composition comprising a conjugate as described herein in combination with a pharmaceutically acceptable excipient. The compositions encompass all types of formulations and in particular those that are suited for injection such as powders that can be reconstituted, as well as liquids (e.g., suspensions and solutions).

In one or more embodiments of the invention, a method for administering an EPO conjugate is provided, the method comprising the step of administering to a patient in need thereof a composition comprising one or more conjugates as described herein, wherein the composition contains a therapeutically effective amount of the one or more conjugates. The step of administering the conjugate can be effected by injection (e.g., intramuscular injection, intravenous injection, subcutaneous injection, and so forth). The patient may be one suffering from anemia, e.g., due to chronic renal failure, or AIDS, or as a result of chemotherapy. In one or more particular embodiments of a method for administering, the conjugate-comprising composition is administered once daily, every other day, twice a week, three times a week, once a week, once every other week, once every three weeks, or even one a month.

Each of the herein-described features of the invention is meant to apply equally to each and every embodiment as described herein, unless otherwise indicated.

Additional objects, advantages and novel features of the invention will be set forth in the description that follows, and in part, will become apparent to those skilled in the art upon reading the following, or may be learned by practice of the invention.

DETAILED DESCRIPTION OF THE INVENTION

Figure 1A:
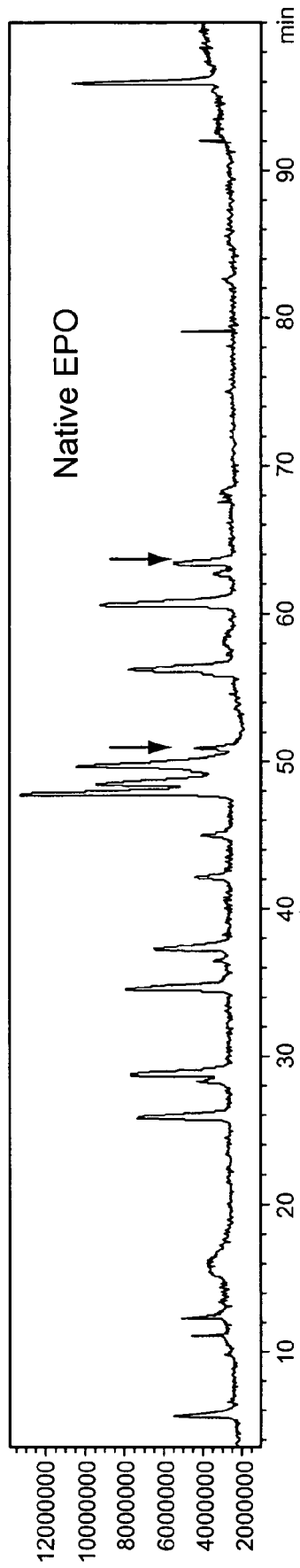
FIGS. 1A-1D correspond to peptide mapping results for unmodified EPO, along with exemplary PEG-EPO conjugate samples as described in Example 18. Plots correspond to total ion current based upon electrospray ionization mass spectrometric detection.
Figure 1B:
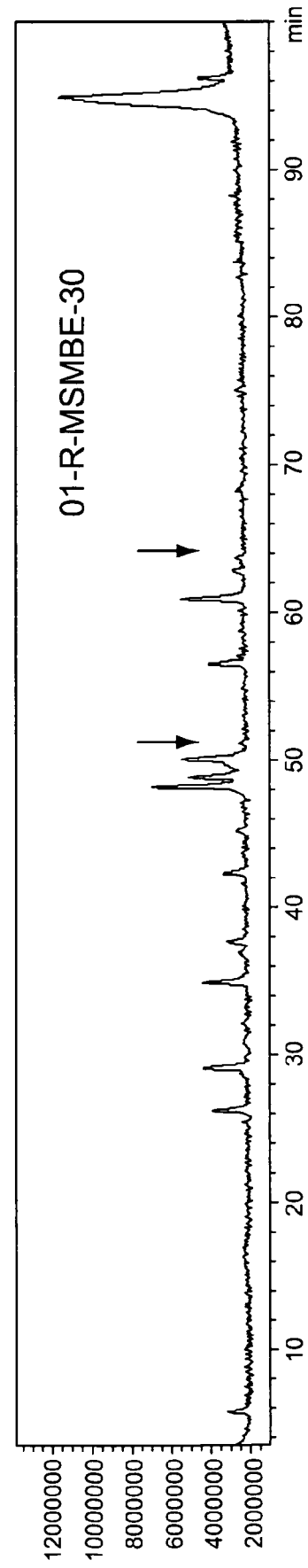
Figure 1C:
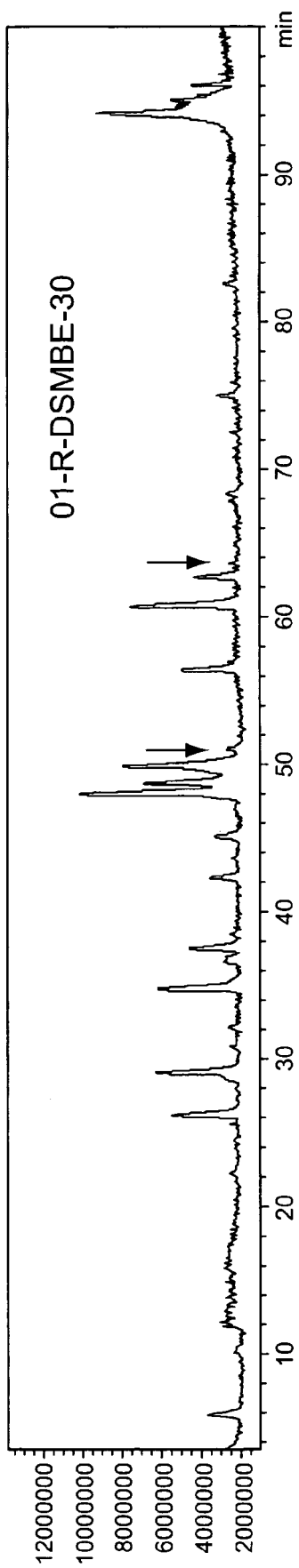
Figure 1D:
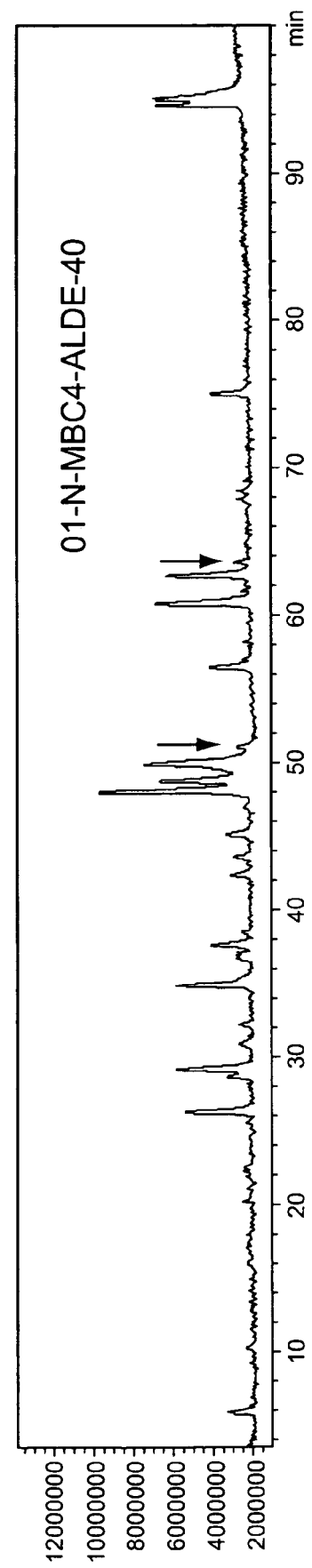

Before describing one or more embodiments of the present invention in detail, it is to be understood that this invention is not limited to the particular polymers, synthetic techniques, EPO moieties, and the like, as such may vary.

It must be noted that, as used in this specification and the intended claims, the singular forms "a," "an," and "the" include plural referents unless the context clearly dictates otherwise. Thus, for example, reference to "a polymer"

includes a single polymer as well as two or more of the same or different polymers, reference to "an optional excipient" refers to a single optional excipient as well as two or more of the same or different optional excipients, and the like.

In describing and claiming one or more embodiments of the present invention, the following terminology will be used in accordance with the definitions described below.

"PEG," "polyethylene glycol" and "poly(ethylene glycol)" as used herein, are interchangeable and meant to encompass any non-peptidic water-soluble poly(ethylene oxide). Typically, PEGs for use in accordance with the invention comprise the following structure "—(OCH$_2$CH$_2$)$_n$—" where (n) is 2 to 4000, preferably from 200 to 1400. As used herein, PEG also includes "—CH$_2$CH$_2$—O(CH$_2$CH$_2$O), —CH$_2$CH$_2$-" and "—(OCH$_2$CH$_2$)$_n$O—," depending upon whether or not the terminal oxygens have been displaced. Throughout the specification and claims, it should be remembered that the term "PEG" includes structures having various terminal or "end capping" groups and so forth. The term "PEG" also means a polymer that contains a majority, that is to say, greater than 50%, of —OCH$_2$CH$_2$— repeating subunits. With respect to specific forms, the PEG can take any number of a variety of molecular weights, as well as structures or geometries such as "branched," "linear," "forked," "multifunctional," and the like, to be described in greater detail below.

The terms "end-capped" and "terminally capped" are interchangeably used herein to refer to a terminal or endpoint of a polymer having an end-capping moiety. Typically, although not necessarily, the end-capping moiety comprises a hydroxy or C$_{1-20}$ alkoxy group, more preferably a C$_{1-10}$ alkoxy group, and still more preferably a C$_{1-5}$ alkoxy group. Thus, examples of end-capping moieties include alkoxy (e.g., methoxy, ethoxy and benzyloxy), as well as aryl, heteroaryl, cyclo, heterocyclo, and the like. It must be remembered that the end-capping moiety may include one or more atoms of the terminal monomer in the polymer [e.g., the end-capping moiety "methoxy" in CH$_3$O(CH$_2$CH$_2$O)$_n$— and CH$_3$(OCH$_2$CH$_2$)$_n$—]. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) to which the polymer is coupled can be determined by using a suitable detector. Such labels include, without limitation, fluorescers, chemiluminescers, moieties used in enzyme labeling, calorimetric (e.g., dyes), metal ions, radioactive moieties, and the like. Suitable detectors include photometers, films, spectrometers, and the like. The end-capping group can also advantageously comprise a phospholipid. When the polymer has an end-capping group comprising a phospholipid, unique properties are imparted to the polymer and the resulting conjugate. Exemplary phospholipids include, without limitation, those selected from the class of phospholipids called phosphatidylcholines. Specific phospholipids include, without limitation, those selected from the group consisting of dilauroylphosphatidylcholine, dioleylphosphatidylcholine, dipalmitoylphosphatidylcholine, disteroylphosphatidylcholine, behenoylphosphatidylcholine, arachidoylphosphatidylcholine, and lecithin.

"Non-naturally occurring" with respect to a polymer as described herein, means a polymer that in its entirety is not found in nature. A non-naturally occurring polymer may, however, contain one or more monomers or segments of monomers that are naturally occurring, so long as the overall polymer structure is not found in nature.

The term "water-soluble" as in a "water-soluble polymer" is any polymer that is soluble in water at room temperature. Typically, a water-soluble polymer will transmit at least about 75%, more preferably at least about 95%, of light transmitted by the same solution after filtering. On a weight basis, a water-soluble polymer will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer is about 95% (by weight) soluble in water or completely soluble in water.

Molecular weight in the context of a water-soluble polymer, such as PEG, can be expressed as either a number average molecular weight or a weight average molecular weight. Unless otherwise indicated, all references to molecular weight herein refer to the weight average molecular weight. Both molecular weight determinations, number average and weight average, can be measured using gel permeation chromatography or other liquid chromatography techniques. Other methods for measuring molecular weight values can also be used, such as the use of end-group analysis or the measurement of colligative properties (e.g., freezing-point depression, boiling-point elevation, or osmotic pressure) to determine number average molecular weight or the use of light scattering techniques, ultracentrifugation or viscometry to determine weight average molecular weight. The polymers are typically polydisperse (i.e., number average molecular weight and weight average molecular weight of the polymers are not equal), possessing low polydispersity values of preferably less than about 1.2, more preferably less than about 1.15, still more preferably less than about 1.10, yet still more preferably less than about 1.05, and most preferably less than about 1.03.

The term "active" or "activated" when used in conjunction with a particular functional group, refers to a reactive functional group that reacts readily with an electrophile or a nucleophile on another molecule. This is in contrast to those groups that require strong catalysts or highly impractical reaction conditions in order to react (i.e., a "non-reactive" or "inert" group).

As used herein, the term "functional group" or any synonym thereof is meant to encompass protected forms thereof as well as unprotected forms.

A leaving group is an atom or molecule (charged or uncharged) that is displaced from a parent molecule, e.g., in a substitution or an elimination reaction.

The terms "spacer moiety," "linkage" and "linker" are used herein to refer to an atom or a collection of atoms optionally used to link interconnecting moieties such as a terminus of a polymer segment and an EPO moiety or an electrophile or nucleophile of an EPO moiety. The spacer moiety may be hydrolytically stable or may include a physiologically hydrolyzable or enzymatically degradable linkage. Preferably, a spacer or linker in the present invention is one that is hydrolytically stable.

"Alkyl" refers to a hydrocarbon chain, typically ranging from about 1 to 15 atoms in length. Such hydrocarbon chains are preferably but not necessarily saturated and may be branched or straight chain, although typically straight chain is preferred. Exemplary alkyl groups include methyl, ethyl, propyl, butyl, pentyl, 1-methylbutyl, 1-ethylpropyl, 3-methylpentyl, and the like. As used herein, "alkyl" includes cycloalkyl as well as cycloalkylene-containing alkyl.

"Lower alkyl" refers to an alkyl group containing from 1 to 6 carbon atoms, and may be straight chain or branched, as exemplified by methyl, ethyl, n-butyl, i-butyl, and t-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8 carbon atoms. "Cycloalkylene" refers to a cycloalkyl group that is inserted into an alkyl chain by bonding of the chain at any two carbons in the cyclic ring system.

"Alkoxy" refers to an —O—R group, wherein R is alkyl or substituted alkyl, preferably $C_{1-6}$ alkyl (e.g., methoxy, ethoxy, propyloxy, and so forth).

The term "substituted" as in, for example, "substituted alkyl," refers to a moiety (e.g., an alkyl group) substituted with one or more noninterfering substituents, such as, but not limited to: alkyl, $C_{3-8}$ cycloalkyl, e.g., cyclopropyl, cyclobutyl, and the like; halo, e.g., fluoro, chloro, bromo, and iodo; cyano; alkoxy, lower phenyl; substituted phenyl; and the like. "Substituted aryl" is aryl having one or more noninterfering groups as a substituent. For substitutions on a phenyl ring, the substituents may be in any orientation (i.e., ortho, meta, or para).

"Noninterfering substituents" are those groups that, when present in a molecule, are typically nonreactive with other functional groups contained within the molecule.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably sulfur, oxygen, or nitrogen, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom that is not a carbon. Preferred heteroatoms include sulfur, oxygen, and nitrogen.

"Substituted heteroaryl" is heteroaryl having one or more noninterfering groups as substituents.

"Substituted heterocycle" is a heterocycle having one or more side chains formed from noninterfering substituents.

"Electrophile" and "electrophilic group" refer to an ion or atom or collection of atoms, that may be ionic, having an electrophilic center, i.e., a center that is electron seeking, capable of reacting with a nucleophile.

"Nucleophile" and "nucleophilic group" refers to an ion or atom or collection of atoms that may be ionic having a nucleophilic center, i.e., a center that is seeking an electrophilic center or with an electrophile.

"Atom length" refers to the number of atoms making up a particular fragment, spacer, linker or the like. By atom length is meant the number of atoms in a single chain, not counting substituents. For instance, —$CH_2$— counts as one atom with respect to atom length, —$CH_2CH_2O$— counts as 3 atoms in length, and so on.

A "physiologically cleavable" or "hydrolyzable" or "degradable" bond is a bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides and oligonucleotides.

An "enzymatically degradable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include, but are not limited to, the following: carbon-carbon bonds (e.g., in aliphatic chains), ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

"Pharmaceutically acceptable excipient or carrier" refers to an excipient that may optionally be included in the compositions of the invention and that causes no significant adverse toxicological effects to the patient. "Pharmacologically effective amount," "physiologically effective amount," and "therapeutically effective amount" are used interchangeably herein to mean the amount of a polymer-(EPO) moiety conjugate that is needed to provide a desired level of the conjugate (or corresponding unconjugated EPO moiety) in the bloodstream or in the target tissue. The precise amount will depend upon numerous factors, e.g., the particular EPO moiety, the components and physical characteristics of the therapeutic composition, intended patient population, individual patient considerations, and the like, and can readily be determined by one skilled in the art, based upon the information provided herein.

"Multi-functional" means a polymer having three or more functional groups contained therein, where the functional groups may be the same or different. Multi-functional polymeric reagents of the invention will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer backbone.

The term "EPO moiety," or simply "EPO" as used herein, refers to a moiety having EPO activity, i.e., that ability, in-vivo, to stimulate red blood cell production as welt as the division and differentiation of committed erythroid progenitors in the bone marrow to cause bone marrow cells to increase the production of reticulocytes and red blood cells. The EPO moiety will also have at least one electrophilic group or nucleophilic group suitable for reaction with a polymeric reagent. In addition, the term "EPO moiety" or "EPO" encompasses both the EPO moiety prior to conjugation as well as the EPO moiety residue following conjugation. As will be explained in further detail below, one of ordinary skill in the art can determine whether any given moiety has EPO activity. A protein having the amino acid sequence corresponding to SEQ ID NO: 1 or SEQ ID NO: 2 is an EPO moiety in accordance with the invention, as well as any protein or polypeptide substantially homologous thereto, whose biological properties result in the stimulation of red blood cell production and in the stimulation of the division and differentiation of committed erythroid progenitors in the bone marrow. As used herein, the term "EPO moiety" includes fragments and EPO modified deliberately, as for example, by site directed mutagenesis or accidentally through mutations. These terms also include analogs having from 1 to 6 additional glycosylation sites, analogs having at least one additional amino acid at the carboxy terminal end of the protein wherein the additional amino acid(s) includes at least one glycosylation site, and analogs having an amino acid sequence which includes a rearrangement of at least one glycosylation site, such as for example the analogs disclosed in European Patent Publication No. 640 619. These terms include both natural and recombinantly produced human erythropoietin.

The term "substantially homologous" means that a particular subject sequence, for example, a mutant sequence, varies from a reference sequence by one or more substitutions, deletions, or additions, the net effect of which does not result in an adverse functional dissimilarity between the reference and subject sequences. For purposes of the present invention, sequences having greater than 95 percent homology, equivalent biological properties, and equivalent expression characteristics are considered substantially homologous. For purposes of determining homology, truncation of the mature sequence should be disregarded. Sequences having lesser degrees of homology, comparable bioactivity, and equivalent expression characteristics are considered substantial equivalents.

The term "fragment" of the EPO protein means any protein or polypeptide having the amino acid sequence of a portion or fragment of an EPO protein, and which has the biological activity of the EPO. Fragments include proteins or polypeptides produced by proteolytic degradation of the EPO protein or produced by chemical synthesis by methods routine in the art. An EPO protein or fragment thereof is biologically active when administration of the protein or fragment to a human results in the stimulation of red blood cell production and the stimulation of the division and differentiation of committed erythroid progenitors in the bone marrow. Determining such biological activity of the EPO protein can carried out by conventional, well-known tests utilized for such purposes on one or more species of mammals. An appropriate test which can be utilized to demonstrate such biological activity is described herein.

The term "patient," or "subject" refers to a living organism suffering from or prone to a condition that can be prevented or treated by administration of an EPO moiety (e.g., conjugate), and includes both humans and animals.

"Optional" or "optionally" means that the subsequently described circumstance may or may not occur, so that the description includes instances where the circumstance occurs and instances where it does not.

"Substantially" means nearly totally or completely, for instance, satisfying one or more of the following: greater than 50%, 51% or greater, 75% or greater, 80% or greater, 90% or greater, and 95% or greater of the condition.

"Minority" as used herein, means less than 50% of a given population. For instance, a population of polymer conjugates, where a minority of such conjugates have polymer attached at a given EPO amino acid site, refers to an overall population of polymer conjugates, which may or may not be more precisely defined, where 50% or less of the defined population has polymer attached at a given EPO amino acid site. Specific exemplary minority amounts include less than 50%, less than 40%, less than 30%, less than 25%, less than 20%, less than 15%, or even less than 10% of a given population.

"Ambient" in reference to temperature, refers to the temperature of the air in a particular environment, also referred to synonomously as "room temperature". Room temperature typically refers to a temperature in a range from about 16° C. to about 25° C.

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G.

Turning to one or more embodiments of the invention, a conjugate is provided, the conjugate comprising an EPO moiety covalently attached, either directly or through a spacer moiety, to a non-peptidic water-soluble polymer. The conjugates of the invention will possess one or more of the following features.

The EPO Moiety

As previously stated, the conjugate comprises an EPO moiety (also referred to herein simply as "EPO") covalently attached, either directly or through a spacer moiety, to a non-peptidic water-soluble polymer. As used herein, the term "EPO moiety" shall refer to the EPO moiety prior to conjugation as well as to the EPO moiety following attachment to a non-peptidic water-soluble polymer. In the latter instance, EPO is often referred to as a residue of erythropoietin or as an EPO residue, since the parent EPO moiety itself is slightly altered from the unmodified parent, due to the covalent attachment of one or more water-soluble polymers thereto. The EPO moiety in the conjugate is any peptide that provides an erythropoietic effect in vivo or in vitro.

The cDNA coding for human EPO has been isolated and characterized. See, for example, U.S. Pat. No. 4,703,008. The amino acid sequence for recombinant human EPO ("rHuEPO") is identical to the sequence for EPO obtained from human urinary sources. The amino acid sequence for human EPO is provided in SEQ ID NO: 1. An arginine residue-containing form of EPO is provided in SEQ ID NO: 2. EPO can be expressed in bacterial (e.g., *Escherichia coli*), mammalian (e.g., Chinese hamster ovary cells), and yeast (e.g., *Saccharomyces cerevisiae*) expression systems, among others.

For any given moiety, it is possible to determine whether that moiety has EPO activity. For example, as described in U.S. Pat. No. 5,688,679, an EPO moiety of interest can be evaluated for EPO activity by observing the formation of erythroid colonies in a culture of mouse bone marrow cells in a plasma clot. Briefly, as described in U.S. Pat. No. 5,688,679, the EPO moiety of interest is first added to the culture. After incubation for 36 to 48 hours, the plasma clots can be fixed on microscope slides, stained with benzidine for hemoglobin, and erythroid colonies counted. The tested EPO moiety will have erythropoietic activity if there are a greater number of erythroid colonies in the EPO-moiety treated culture than in a control.

Additional illustrative in vitro assays for evaluating dose-dependent proliferation activities of an EPO moiety (or an EPO moiety conjugate) include those using EPO-responsive target cells such as primary murine spleen cells (Krystal, G., 1983, *Exp. Hematol.* 11, 649-60), HCD 57, a murine MEL cell line (Hankins, W. D., et al., 1987, *Blood*, 70, 173a), and UT7-EPO, a human cell line derived from the bone marrow of a patient with acute megakaryoblastic leukemia (Komatsu, N., et al., 1991, *Cancer Res.* 51, 341-348).

Alternatively, EPO activity can be evaluated in vivo in rats by monitoring changes in reticulocyte counts and hemoglobin levels after a single tail vein injection of a particular EPO moiety (or corresponding conjugate). In vivo activity can also be measured using the normocythaemic mouse assay (European Pharmacopoia 2002).

Nonlimiting examples of EPO moieties include the following: EPO as identified in SEQ. ID. NO: 1 and SEQ. ID. NO: 2, as well as truncated versions, hybrid variants, and peptide mimetics thereof. Biologically active fragments, deletion variants, substitution variants or addition variants of any of the foregoing that maintain at least some degree of EPO activity can also serve as an EPO moiety.

Depending on the system used to express proteins having EPO activity, the EPO moiety can be unglycosylated or glycosylated and either may be used. That is, the EPO moiety can be unglycosylated or the EPO moiety can be glycosylated. In one or more embodiments of the invention, it is preferred that the EPO moiety is not glycosylated.

The EPO moiety can advantageously be modified to include one or more amino acid residues such as, for example, lysine, cysteine and/or arginine, in order to provide facile attachment of the polymer to an atom within the side chain of the amino acid. In addition, the EPO moiety can be modified to include a non-naturally occurring amino acid residue. Techniques for adding amino acid residues and non-naturally occurring amino acid residues are well known to those of ordinary skill in the art. Reference is made to the following: Roe, B., et al., Ed., "Protocols for Recombinant DNA Isolation, Cloning and Sequencing", 1996, Wiley & Sons.; Ausubel, F. M., Ed., "Short Protocols in Molecular Biology", 5$^{th}$ Ed., Wiley & Sons; J. March, "Advanced Organic Chemistry: Reactions Mechanisms and Structure", 4th Ed. (New York: Wiley-Interscience, 1992); Wen, D., et al., J. Biol. Chem, 1994, 269 (36), 22839. In one or more embodiments of the invention, it is preferred that the EPO moiety is not modified to include one or more amino acid residues.

In addition, the EPO moiety can advantageously be modified to include attachment of a functional group (other than through addition of a functional group-containing amino acid residue). In addition, the EPO moiety can be modified to include an N-terminal alpha carbon. In addition, the EPO moiety can be modified to include one or more carbohydrate moieties. In some embodiments of the invention, it is preferred that the EPO moiety is not modified to include a thiol group and/or an N-terminal alpha carbon.

The EPO moiety can be obtained from any conventional source such as tissues, protein synthesis, or cell culture with natural or recombinant cells. Preferred are recombinant methods. Briefly, recombinant methods involve constructing the nucleic acid encoding the desired polypeptide or fragment, cloning the nucleic acid into an expression vector, transforming a host cell (e.g., plant, bacteria, yeast, transgenic animal cell, or mammalian cell such as Chinese hamster ovary cell or baby hamster kidney cell), and expressing the nucleic acid to produce the desired polypeptide or fragment. Methods for producing and expressing recombinant polypeptides in vitro and in prokaryotic and eukaryotic host cells are known to those of ordinary skill in the art, and are disclosed, for example, in U.S. Pat. Nos. 5,733,761, 5,641,670, and 5,733,746, among others.

To facilitate identification and purification of the recombinant polypeptide, nucleic acid sequences that encode for an epitope tag or other affinity binding sequence can be inserted or added in-frame with the coding sequence, thereby producing a fusion protein comprised of the desired polypeptide and a polypeptide suited for binding. Fusion proteins can be identified and purified by first running a mixture containing the fusion protein through an affinity column bearing binding moieties (e.g., antibodies) directed against the epitope tag or other binding sequence in the fusion proteins, thereby binding the fusion protein within the column. Thereafter, the fusion protein can be recovered by washing the column with the appropriate solution (e.g., acid) to release the bound fusion protein. The recombinant polypeptide can also be identified and purified by lysing the host cells, separating the polypeptide, e.g., by size exclusion chromatography, and collecting the polypeptide. These and other methods for identifying and purifying recombinant polypeptides are known to those of ordinary skill in the art. In one or more embodiments of the invention, however, it is preferred that the EPO moiety is not in the form of a fusion protein.

A preferred EPO moiety has the amino acid sequence as provided in SEQ ID NO: 1. Unless specifically noted, all assignments of a numeric location of an amino acid residue as provided herein are based on SEQ ID NO: 1. An additionally described amino acid sequence that corresponds to another EPO moiety is provided in SEQ ID NO: 2. Commercially available versions of EPO moieties are available such as PROCLAT® EPO (Dragon Pharmaceuticals, Inc., Vancouver, B. C., Canada), EPOX EPO (Mumbai, India), human cell-expressed recombinant human EPO (Apollo Cytokine Research), ARANESP®, and PROCRIT® EPO (Ortho Biotech Products, L. P., (Bridgewater, N.J.).

The Non-peptidic Water-Soluble Polymer

As previously discussed, each conjugate comprises an EPO moiety attached to a non-peptidic water-soluble polymer. With respect to the non-peptidic water-soluble polymer, the non-peptidic water-soluble polymer is non-peptidic, non-toxic, non-naturally occurring and biocompatible. With respect to biocompatibility, a substance is considered biocompatible if the beneficial effects associated with use of the substance alone or with another substance (e.g., an active agent such as an EPO moiety) in connection with living tissues (e.g., administration to a patient) outweighs any deleterious effects as evaluated by a clinician, e.g., a physician. With respect to non-immunogenicity, a substance is considered nonimmunogenic if the intended use of the substance in vivo does not produce an undesired immune response (e.g., the formation of antibodies) or, if an immune response is produced, that such a response is not deemed clinically significant or important as evaluated by a clinician. It is particularly preferred that the non-peptidic water-soluble polymer is biocompatible and nonimmunogenic.

Further, the polymer is typically characterized as having from 2 to about 300 termini. Examples of such polymers include, but are not limited to, poly(alkylene glycols) such as polyethylene glycol (PEG), poly(propylene glycol) ("PPG"), copolymers of ethylene glycol and propylene glycol and the like, poly(oxyethylated polyol), poly(olefinic alcohol), poly (vinylpyrrolidone), poly(hydroxyalkylmethacrylamide), poly(hydroxyalkylmethacrylate), poly(saccharides), poly($\alpha$-hydroxy acid), poly(vinyl alcohol), polyphosphazene, polyoxazoline, poly(N-acryloylmorpholine), and combinations of any of the foregoing.

The polymer is not limited to a particular structure and can be linear (e.g., alkoxy PEG or bifunctional PEG), branched or multi-armed (e.g., forked PEG or PEG attached to a polyol core), dendritic, or with degradable linkages. Moreover, the internal structure of the polymer can be organized in any number of different patterns and can be selected from the group consisting of homopolymer, alternating copolymer, random copolymer, block copolymer, alternating tripolymer, random tripolymer, and block tripolymer.

Typically, activated PEG and other activated water-soluble polymers (i.e., polymeric reagents) are activated with a suitable activating group appropriate for coupling to a desired site on the EPO moiety. Thus, a polymeric reagent will possess a reactive group for reaction with the EPO moiety. Representative polymeric reagents and methods for conjugating these polymers to an active moiety are known in the art and further described in Zalipsky, S., et al., "Use of Functionalized Poly (*Ethylene Glycols*) *for Modification of Polypeptides*" in Polyethylene Glycol Chemistry: Biotechnical and Biomedical Applications, J. M. Harris, Plenus Press, New York (1992), and in Zalipsky (1995) *Advanced Drug Reviews* 16:157-182.

Typically, the weight-average molecular weight of the non-peptidic water-soluble polymer in the conjugate is from about 100 Daltons to about 150,000 Daltons. Exemplary ranges, however, include weight-average molecular weights in the range of greater than 5,000 Daltons to about 100,000 Daltons, in the range of from about 6,000 Daltons to about 90,000 Daltons, in the range of from about 10,000 Daltons to about 85,000 Daltons, in the range of greater than 10,000 Daltons to about 60,000 Daltons, in the range of from about 20,000 Daltons to about 85,000 Daltons, in the range of from about 53,000 Daltons to about 85,000 Daltons, in the range of from about 25,000 Daltons to about 120,000 Daltons, in the range of from about 29,000 Daltons to about 120,000 Daltons, in the range of from about 35,000 Daltons to about 120,000 Daltons, and in the range of from about 40,000 Daltons to about 120,000 Daltons. For any given non-peptidic water-soluble polymer, PEGs having a molecular weight in one or more of these ranges are preferred.

Exemplary weight-average molecular weights for the non-peptidic water-soluble polymer include about 100 Daltons, about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 1,500 Daltons, about 2,000 Daltons, about 2,200 Daltons, about 2,500 Daltons, about 3,000 Daltons, about 4,000 Daltons, about 4,400 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons. Branched versions of the water-soluble polymer (e.g., a branched 40,000 Dalton water-soluble polymer comprised of two 20,000 Dalton polymers) having a total molecular weight of any of the foregoing can also be used. In one or more embodiments, the conjugate will not have any PEG moieties attached, either directly or indirectly, with a PEG having a weight average molecular weight of less than about 6,000 Daltons.

When used as the polymer, PEG will typically comprise a number of (—OCH$_2$ CH$_2$—) monomers [or (—CH$_2$CH$_2$O—) monomers, depending on how the PEG is defined]. As used throughout the description, the number of repeating units is identified by the subscript "n" in "(OCH$_2$CH$_2$)$_n$." Thus, the value of (n) typically falls within one or more of the following ranges: from 2 to about 3400, from about 100 to about 2300, from about 100 to about 2270, from about 136 to about 2050, from about 200 to about 1400, from about 225 to about 1930, from about 450 to about 1930, from about 1200 to about 1930, from about 568 to about 2727, from about 660 to about 2730, from about 795 to about 2730, from about 795 to about 2730, from about 909 to about 2730, and from about 1,200 to about 1,900. For any given polymer in which the molecular weight is known, it is possible to determine the number of repeating units (i.e., "n") by dividing the total weight-average molecular weight of the polymer by the molecular weight of the repeating monomer.

One particularly preferred polymer for use in the invention is an end-capped polymer, that is, a polymer having at least one terminus capped with a relatively inert group, such as a lower C$_{1-6}$ alkoxy group, although a hydroxyl group can also be used. When the polymer is PEG, for example, it is preferred to use a methoxy-PEG (commonly referred to as mPEG), which is a linear form of PEG wherein one terminus of the polymer is a methoxy (—OCH$_3$) group, while the other terminus is a hydroxyl or other functional group that can be optionally chemically modified.

In one form useful in one or more embodiments of the present invention, free or unbound PEG is a linear polymer terminated at each end with hydroxyl groups:

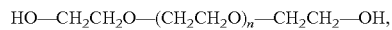

wherein (n) typically ranges from zero to about 4,000.

The above polymer, alpha-, omega-dihydroxylpoly(ethylene glycol), can be represented in brief form as HO-PEG-OH where it is understood that the —PEG-symbol can represent the following structural unit:

wherein (n) is as defined as above.

Another type of PEG useful in one or more embodiments of the present invention is methoxy-PEG-OH, or mPEG in brief, in which one terminus is the relatively inert methoxy group, while the other terminus is a hydroxyl group. The structure of mPEG is given below.

wherein (n) is as described above.

Multi-armed or branched PEG molecules, such as those described in U.S. Pat. No. 5,932,462, can also be used as the PEG polymer. For example, PEG can comprise the structure:

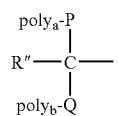

wherein:
poly$_a$ and poly$_b$ are PEG backbones (either the same or different), such as methoxy poly(ethylene glycol);
R" is a nonreactive moiety, such as H, methyl or a PEG backbone; and
P and Q are nonreactive linkages. In a preferred embodiment, the branched PEG polymer is methoxy poly(ethylene glycol) disubstituted lysine. Depending on the specific EPO moiety used, the reactive ester functional group of the disubstituted lysine may be further modified to form a functional group suitable for reaction with the target group within the EPO moiety.

In addition, the PEG can comprise a forked PEG. An example of a forked PEG is represented by the following structure:

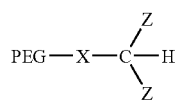

wherein: X is a spacer moiety of one or more atoms and each Z is an activated terminal group linked to CH by a chain of atoms of defined length. International Patent Application No.

PCT/US99/05333 discloses various forked PEG structures capable of use in one or more embodiments of the present invention. The chain of atoms linking the Z functional groups to the branching carbon atom serve as a tethering group and may comprise, for example, alkyl chains, ether chains, ester chains, amide chains and combinations thereof.

The PEG polymer may comprise a pendant PEG molecule having reactive groups, such as carboxyl, covalently attached along the length of the PEG rather than at the end of the PEG chain. The pendant reactive groups can be attached to the PEG directly or through a spacer moiety, such as an alkylene group.

In addition to the above-described forms of PEG, the polymer can also be prepared with one or more weak or degradable linkages in the polymer, including any of the above-described polymers. For example, PEG can be prepared with ester linkages in the polymer that are subject to hydrolysis. As shown below, this hydrolysis results in cleavage of the polymer into fragments of lower molecular weight:

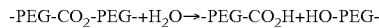
-PEG-CO$_2$-PEG-+H$_2$O→-PEG-CO$_2$H+HO-PEG-

Other hydrolytically degradable linkages, useful as a degradable linkage within a polymer backbone, include: carbonate linkages; imine linkages resulting, for example, from reaction of an amine and an aldehyde (see, e.g., Ouchi et al. (1997) *Polymer Preprints* 38(1):582-3); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; orthoester linkages that are, for example, formed by reaction between a formate and an alcohol; amide linkages formed by an amine group, e.g., at an end of a polymer such as PEG, and a carboxyl group of another PEG chain; urethane linkages formed from reaction of, e.g., a PEG with a terminal isocyanate group and a PEG alcohol; peptide linkages formed by an amine group, e.g., at an end of a polymer such as PEG, and a carboxyl group of a peptide; and oligonucleotide linkages formed by, for example, a phosphoramidite group, e.g., at the end of a polymer, and a 5' hydroxyl group of an oligonucleotide.

Such optional features of the conjugate, i.e., the introduction of one or more degradable linkages into the polymer chain, may provide for additional control over the final desired pharmacological properties of the conjugate upon administration. For example, a large and relatively inert conjugate (i.e., having one or more high molecular weight PEG chains attached thereto, for example, one or more PEG chains having a molecular weight greater than about 10,000, wherein the conjugate possesses essentially no bioactivity) may be administered, which is then hydrolyzed in vivo to generate a bioactive conjugate possessing a portion of the original PEG chain. In this way, the properties of the conjugate can be more effectively tailored to balance the bioactivity and circulating half-life of the conjugate over time.

The water-soluble polymer associated with the conjugate can also be "cleavable." That is, the water-soluble polymer cleaves (either through hydrolysis, enzymatic processes, or otherwise), thereby resulting in the unconjugated EPO moiety. In some instances, cleavable polymers detach from the EPO moiety in vivo without leaving any fragment of the water-soluble polymer. In other instances, cleavable polymers detach from the EPO moiety in vivo leaving a relatively small fragment (e.g., a succinate tag) from the water-soluble polymer. An exemplary cleavable polymer includes one that attaches to the EPO moiety via a carbonate linkage.

Those of ordinary skill in the art will recognize that the foregoing discussion concerning non-peptidic and water-soluble polymers by no means exhaustive and is merely illustrative, and that all polymeric materials having the qualities described above are contemplated. As used herein, the term "polymeric reagent" generally refers to an entire molecule, which can comprise a water-soluble polymer segment, an optional spacer or linker moiety, and a functional group.

As described above, a conjugate of the invention comprises a water-soluble polymer covalently attached to an EPO moiety. Typically, for any given conjugate, there will be one to three water-soluble polymers covalently attached to one or more moieties having EPO activity. In some instances, however, the conjugate may have 1, 2, 3, 4, 5, 6, 7, 8 or more water-soluble polymers individually attached to an EPO moiety.

The particular linkage within the moiety having EPO activity and the polymer depends on a number of factors. Such factors include, for example, the particular linkage chemistry employed, the particular EPO moiety, the available functional groups within the EPO moiety (either for attachment to a polymer or conversion to a suitable attachment site), the presence of additional reactive functional groups within the EPO moiety, and the like.

The conjugates of the invention can be, although not necessarily, prodrugs, meaning that the linkage between the polymer and the EPO moiety is hydrolytically degradable to allow release of the parent moiety. Exemplary degradable linkages include carboxylate ester, phosphate ester, thiolester, anhydrides, acetals, ketals, acyloxyalkyl ether, imines, orthoesters, peptides and oligonucleotides. Such linkages can be readily prepared by appropriate modification of either the EPO moiety (e.g., the carboxyl group C terminus of the protein or a side chain hydroxyl group of an amino acid such as serine or threonine contained within the protein) and/or the polymeric reagent using coupling methods commonly employed in the art. Most preferred, however, are hydrolyzable linkages that are readily formed by reaction of a suitably activated polymer with a non-modified functional group contained within the moiety having EPO activity.

Alternatively, a hydrolytically stable linkage, such as an amide, urethane (also known as carbamate), amine, thioether (also known as sulfide), or urea (also known as carbamide) linkage can also be employed as the linkage for coupling the EPO moiety. Again, a preferred hydrolytically stable linkage is an amide. In one approach, a water-soluble polymer bearing an activated ester can be reacted with an amine group on the EPO moiety to thereby result in an amide linkage.

The conjugates (as opposed to an unconjugated EPO moiety) may or may not possess a measurable degree of EPO activity. That is to say, a polymer-EPO moiety conjugate in accordance with the invention will possesses anywhere from about 0.1% to about 100% of the bioactivity of the unmodified parent EPO moiety. In some instances, the polymer-EPO moiety conjugates may posses greater than 100% bioactivity of the unmodified parent EPO moiety. Preferably, compounds possessing little or no EPO activity typically contain a hydrolyzable linkage connecting the polymer to the moiety, so that regardless of the lack of activity in the conjugate, the active parent molecule (or a derivative thereof) is released upon aqueous-induced cleavage of the hydrolyzable linkage. Such activity may be determined using a suitable in vivo or in vitro model, depending upon the known activity of the particular moiety having EPO activity employed.

For conjugates possessing a hydrolytically stable linkage that couples the moiety having EPO activity to the polymer, the conjugate will typically possess a measurable degree of bioactivity. For instance, such conjugates are typically characterized as having a bioactivity of at least about 2%, 5%, 10%, 15%, 25%, 30%, 40%, 50%, 60%, 80%, 85%, 90%, 95% 97%, 100%, or more relative to that of the unconjugated EPO moiety, when measured in a suitable model, such as those well known in the art. Preferably, conjugates having a hydrolytically stable linkage (e.g., an amide linkage) will possess at least some degree of the bioactivity of the unmodified parent moiety having EPO activity.

Exemplary conjugates in accordance with the invention will now be described wherein the EPO moiety is a protein. Typically, such a protein is expected to share (at least in part) a similar amino acid sequence as human EPO. Thus, while reference will be made to specific locations or atoms within the native human EPO protein, such a reference is for convenience only and one having ordinary skill in the art will be able to readily determine the corresponding location or atom in other moieties having EPO activity. In particular, the description provided herein for native human EPO is often applicable to fragments, deletion variants, substitution variants or addition variants of any of the foregoing.

Amino groups on EPO moieties provide a point of attachment between the EPO moiety and the water-soluble polymer. In one embodiment, the conjugate has one water-soluble conjugate attached at the N-terminal of the EPO moiety, in some instances, however, the composition will contain less than 50% of monoPEGylated conjugates having covalent attachment of the PEG moiety at the N-terminus. Human EPO comprises eight amine-containing lysine residues and one amino terminus (see SEQ ID NO: 1). Thus, exemplary attachment points of this EPO include attachment at the amine-containing side chain associated with a lysine at any one of positions 20, 45, 52, 97, 116, 140, 152 and 154. In some embodiments of the invention, it is preferred that attachment to lysine does not occur at lysine in position 52. In this embodiment, the composition will ideally contain less than 50% of conjugates having attachment at the lysine-52 position. In yet another embodiment, the composition may even be substantially free of such conjugates.

While not wishing to be bound by theory, it is believed that the attachment of a polymer at the lysine-52 position results in a conjugate having reduced or compromised activity. Exemplary attachment points other than the amine-containing side chain associated with lysine-52 include attachment at the amine-containing side chain associated with a lysine at any one of positions 20, 45, 97, 116, 140, 152 and 154. Consequently, these EPO moieties (as well as most any peptidic EPO moiety) have several amines available for participation in conjugating reactions. Covalent attachment of a polymer reagent at lysine 52 can be substantially avoided by the use of a reversible protecting agent such as a cyclic dicarboxylic anhydride. The protecting reagent partially protects the most reactive amino groups in the EPO moiety, such as lysine 52, thereby modifying the profile of conjugates typically formed in a random PEGylation approach.

There are a number of examples of suitable polymeric reagents useful for forming covalent linkages with available amines of an EPO moiety. Specific examples, along with the corresponding conjugate, are provided in Table 1 below. In the table, the variable (n) represents the number of repeating monomeric units (as previously described) and "—NH-(EPO)" or "NH-EPO" represents the residue of the EPO moiety following conjugation to the polymeric reagent. While each polymeric portion [e.g., $(OCH_2CH_2)_n$ or $(CH_2CH_2O)_n$] presented in Table 1 terminates in a "$CH_3$" group, other groups (such as H and benzyl) can be substituted therefor.

TABLE 1

Amine-Specific Polymeric Reagents and the EPO Moiety Conjugate Formed Therefrom

| Polymeric Reagent | Corresponding Conjugate |
|---|---|
| $H_3C-(OCH_2CH_2)_n-O-CH_2CH_2-C(=O)-O-N(\text{succinimidyl})$ <br> mPEG-Succinimidyl Reagent | $H_3C-(OCH_2CH_2)_n-O-CH_2CH_2-C(=O)-NH-(EPO)$ <br> Amide Linkage |
| $H_3CO-(CH_2CH_2O)_n-C(=O)-N(\text{imidazole})$ <br> mPEG-Oxycarbonylimidazole Reagent | $H_3CO-(CH_2CH_2O)_n-C(=O)-NH-(EPO)$ <br> Carbamate Linkage |
| $H_3CO-(CH_2CH_2O)_n-C(=O)-O-C_6H_4-NO_2$ <br> mPEG Nitrophenyl Reagent | $H_3CO-(CH_2CH_2O)_n-C(=O)-NH-(EPO)$ <br> Carbamate Linkage |
| $H_3CO-(CH_2CH_2O)_n-C(=O)-O-C_6H_2Cl_3$ <br> mPEG-Trichlorophenyl Carbonate Reagent | $H_3CO-(CH_2CH_2O)_n-C(=O)-NH-(EPO)$ <br> Carbamate Linkage |
| $H_3C-(OCH_2CH_2)_n-O-CH_2-C(=O)-O-N(\text{succinimidyl})$ <br> mPEG-Succinimidyl Reagent | $H_3C-(OCH_2CH_2)_n-O-CH_2-C(=O)-N-(EPO)$ <br> Amide Linkage |

TABLE 1-continued

Amine-Specific Polymeric Reagents and the EPO Moiety Conjugate Formed Therefrom

| Polymeric Reagent | Corresponding Conjugate |
|---|---|
| Homobifunctional PEG-Succinimidyl Reagent | (EPO)—NH—C(=O)—CH$_2$CH$_2$—(OCH$_2$CH$_2$)$_n$—O—CH$_2$CH$_2$—C(=O)—NH—(EPO)<br>Amide Linkages |
| mPEG-Succinimidyl Reagent: H$_3$CO—(CH$_2$CH$_2$O)$_n$—CH$_2$CH$_2$NH—C(=O)—CH$_2$CH$_2$—C(=O)—O—NHS | H$_3$CO—(CH$_2$CH$_2$O)$_n$—CH$_2$CH$_2$NH—C(=O)—CH$_2$CH$_2$—C(=O)—NH—(EPO)<br>Amide Linkage |
| mPEG Succinimidyl Reagent: H$_3$CO—(CH$_2$CH$_2$O)$_n$—CH$_2$CH$_2$SH—CH$_2$CH$_2$—C(=O)—O—NHS | H$_3$CO—(CH$_2$CH$_2$O)$_n$—CH$_2$CH$_2$SH—CH$_2$CH$_2$—C(=O)—NH—(EPO)<br>Amide Linkage |
| mPEG-Benzotriazole Carbonate Reagent: H$_3$C—(OCH$_2$CH$_2$)$_n$—O—C(=O)—O—Bt | H$_3$C—(OCH$_2$CH$_2$)$_n$—O—C(=O)—NH—(EPO)<br>Carbamate Linkage |
| mPEG-Succinimidyl Reagent: H$_3$C—(OCH$_2$CH$_2$)$_n$—NH—C(=O)—C$_6$H$_4$—C(=O)—O—NHS | H$_3$C—(OCH$_2$CH$_2$)$_n$—NH—C(=O)—C$_6$H$_4$—C(=O)—NH—(EPO)<br>Carbamate Linkage |

TABLE 1-continued

Amine-Specific Polymeric Reagents and the EPO Moiety Conjugate Formed Therefrom

| Polymeric Reagent | Corresponding Conjugate |
|---|---|
| mPEG-Succinimidyl Reagent (H₃CO—(CH₂CH₂O)ₙ—phenyl—O—C(=O)—O—N-succinimidyl) | H₃CO—(CH₂CH₂O)ₙ—phenyl—O—C(=O)—NH—(EPO); Amide Linkage |
| mPEG Succinimidyl Reagent (H₃CO—(CH₂CH₂O)ₙ—O—C(=O)—O—N-succinimidyl) | H₃CO—(CH₂CH₂O)ₙ—C(=O)—O—NH—(EPO); Amide Linkage |
| Branched mPEG2-N-Hydroxysuccinimide Reagent (H₃C—(OCH₂CH₂)ₙ—O—C(=O)—NH—CH₂—CH₂—CH₂—CH(—O—C(=O)—N-succinimidyl)—O—C(=O)—NH—CH₂—(OCH₂CH₂)ₙ—OCH₃) | H₃C—(OCH₂CH₂)ₙ—O—C(=O)—NH—CH₂—CH₂—CH₂—CH(—C(=O)—NH—(EPO))—O—C(=O)—NH—CH₂—(OCH₂CH₂)ₙ—OCH₃; Amide Linkage |
| mPEG-Succinimidyl Reagent (H₃C—(OCH₂CH₂)ₙ—O—CH₂—C(=O)—O—CH(CH₃)—C(=O)—O—N-succinimidyl) | H₃C—(OCH₂CH₂)ₙ—O—CH₂—C(=O)—O—CHCH₃—C(=O)—NH—(EPO); Amide Linkage |
| mPEG-Succinimidyl Reagent (H₃CO—(CH₂CH₂O)ₙ—C(=O)—CH₂CH₂—C(=O)—O—N-succinimidyl) | H₃CO—(CH₂CH₂O)ₙ—C(=O)—CH₂CH₂—C(=O)—NH—(EPO); Amide Linkage |

TABLE 1-continued

Amine-Specific Polymeric Reagents and the EPO Moiety Conjugate Formed Therefrom

| Polymeric Reagent | Corresponding Conjugate |
|---|---|
| $H_3C-(OCH_2CH_2)_n-NH-\overset{O}{\underset{\|}{C}}-O-CH_2$<br>$\phantom{H_3C-(OCH_2CH_2)_n-NH-C-O-}HC-OCH_2-CH_2-CH_2-CH_2-\overset{O}{\underset{\|}{C}}-O-N(\text{succinimide})$<br>$H_3C-(OCH_2CH_2)_n-NH-\overset{O}{\underset{\|}{C}}-O-CH_2$<br>Branched mPEG2-N-Hydroxysuccinimide Reagent | $H_3C-(OCH_2CH_2)_n-NH-\overset{O}{\underset{\|}{C}}-O-CH_2$<br>$\phantom{H_3C-(OCH_2CH_2)_n-NH-C-O-}HC-OCH_2-CH_2-CH_2-CH_2-\overset{O}{\underset{\|}{C}}-NH-(\text{EPO})$<br>$H_3C-(OCH_2CH_2)_n-NH-\overset{O}{\underset{\|}{C}}-O-CH_2$<br>Amide Linkage |
| $H_3C-(OCH_2CH_2)_n-O-CH_2-CH_2-\overset{O}{\underset{\|}{C}}-S-\text{(2-pyridyl)}$<br>mPEG-Thioester Reagent | $H_3C-(OCH_2CH_2)_n-O-CH_2-CH_2-\overset{O}{\underset{\|}{C}}-NH-(\text{EPO})$<br>Amide Linkage (typically to EPO moiety having an N-terminal cysteine or histidine) |
| $\overset{O}{\underset{\|}{HC}}-CH_2CH_2-(OCH_2CH_2)_n-O-CH_2CH_2-CH$<br>Homobifunctional PEG Propionaldehyde Reagent | $NH-CH_2-CH_2-CH_2-(OCH_2CH_2)_n-O-CH_2CH_2-CH_2-NH$<br>$\|\phantom{xxxxxxxxxxxxxxxxxxxxxxxxxxxxxxxxxxxxxxxxxxxxxxxxxxxxxxxx}\|$<br>(EPO) (EPO)<br>Secondary Amine Linkages |
| $H_3C-(OCH_2CH_2)_n-O-CH_2CH_2-CH$<br>$\phantom{H_3C-(OCH_2CH_2)_n-O-CH_2CH_2-}\|\|$<br>$\phantom{H_3C-(OCH_2CH_2)_n-O-CH_2CH_2-CH}O$<br>mPEG Propionaldehyde Reagent | $H_3C-(OCH_2CH_2)_n-O-CH_2CH_2-CH_2-NH-(\text{EPO})$<br>Secondary Amine Linkage |
| $\overset{O}{\underset{\|}{HC}}CH_2CH_2CH_2-(OCH_2CH_2)_n-O-CH_2CH_2CH_2-CH$<br>Homobifunctional PEG Butyraldehyde Reagent | $NH-CH_2CH_2CH_2-(OCH_2CH_2)_n-O-CH_2CH_2CH_2-CH_2-NH$<br>$\|\phantom{xxxxxxxxxxxxxxxxxxxxxxxxxxxxxxxxxxxxxxxxxxxxxxxxxxxxxxxx}\|$<br>(EPO) (EPO)<br>Secondary Amine Linkage |
| $H_3C-(OCH_2CH_2)_n-O-CH_2CH_2CH_2-CH$<br>$\phantom{H_3C-(OCH_2CH_2)_n-O-CH_2CH_2CH_2-}\|\|$<br>$\phantom{H_3C-(OCH_2CH_2)_n-O-CH_2CH_2CH_2-CH}O$<br>mPEG Butyraldehyde Reagent | $H_3C-(OCH_2CH_2)_nO-CH_2CH_2CH_2-CH_2-NH-(\text{EPO})$<br>Secondary Amine Linkage |
| $H_3C-(OCH_2CH_2)_n-O-\overset{O}{\underset{\|}{C}}-NH-(CH_2CH_2O)_4-CH_2CH_2CH_2CH$<br>$\phantom{H_3C-(OCH_2CH_2)_n-O-C-NH-(CH_2CH_2O)_4-CH_2CH_2CH_2-}\|\|$<br>$\phantom{H_3C-(OCH_2CH_2)_n-O-C-NH-(CH_2CH_2O)_4-CH_2CH_2CH_2CH}O$<br>mPEG Butryaldehyde Reagent | $H_3C-(OCH_2CH_2)_n-O-\overset{O}{\underset{\|}{C}}-NH-(CH_2CH_2O)_4-CH_2CH_2CH_2CH_2-NH-(\text{EPO})$<br>Secondary Amine Linkage |

TABLE 1-continued

Amine-Specific Polymeric Reagents and the EPO Moiety Conjugate Formed Therefrom

| Polymeric Reagent | Corresponding Conjugate |
|---|---|
| Homobifunctional PEG Butyraldehyde Reagent: $O=\overset{O}{C}-HN-(CH_2CH_2O)_4-CH_2CH_2CH_2CH$ with $O=\overset{O}{C}-(OCH_2CH_2)_n-O-\overset{O}{C}-NH-(CH_2CH_2O)_4-CH_2CH_2CH_2CH$ | $O=\overset{O}{C}-(OCH_2CH_2)_n-O-\overset{O}{C}-NH-(CH_2CH_2O)_4-CH_2CH_2CH_2-NH-(EPO)$ with $\overset{O}{C}-(CH_2CH_2O)_4-CH_2CH_2CH_2-NH-(EPO)$ HN— Secondary Amine Linkages |
| Branched mPEG2 Butyraldehyde Reagent: $H_3C-(OCH_2CH_2)_n-O-\overset{O}{C}-NH-CH_2-CH_2-CH_2-CH_2$ $H_3C(OCH_2CH_2)_n-O-\overset{O}{C}-NH$ $CH-C-NH-(CH_2CH_2O)_4-CH_2CH_2CH$ | $H_3C-(OCH_2CH_2)_n-O-\overset{O}{C}-NH-CH_2-CH_2-CH_2-CH_2$ $H_3C-(OCH_2CH_2)_n-O-\overset{O}{C}-NH$ $CH-C-NH-(CH_2CH_2O)_4-CH_2CH_2CH_2-NH-(EPO)$ Secondary Amine Linkage |
| Branched mPEG2 Butyraldehyde Reagent: $H_3C-(OCH_2CH_2)_n-NH-\overset{O}{C}-O-CH_2$ $HC-OCH_2-CH_2-CH_2-C-NH-(CH_2CH_2O)_4-CH_2CH_2CH$ $H_3C-(OCH_2CH_2)_n-NH-\overset{O}{C}-O-CH_2$ | $H_3C-(OCH_2CH_2)_n-NH-\overset{O}{C}-O-CH_2$ $HC-OCH_2-CH_2-CH_2-C-NH-(CH_2CH_2O)_4-CH_2CH_2CH_2-NH-(EPO)$ $H_3C-(OCH_2CH_2)_n-NH-\overset{O}{C}-O-CH_2$ Secondary Amine Linkage |
| mPEG Acetal Reagent: $H_3C-(OCH_2CH_2)_n-O-CH_2-CH-OCH_2CH_3$ with $OCH_2CH_3$ | $H_3C-(OCH_2CH_2)_n-O-CH_2CH_2-O-CH_2CH_2-NH-(EPO)$ Secondary Amine Linkage |
| mPEG Piperidone Reagent: $H_3C-(OCH_2CH_2)_n-O-CH_2CH_2-\overset{O}{C}-N$⟨piperidone⟩=O | $H_3C-(OCH_2CH_2)_n-O-CH_2CH_2-\overset{O}{C}-N$⟨piperidine⟩-NH-(EPO) Secondary Amine Linkage (to a secondary carbon) |
| mPEG Methylketone Reagent: $H_3C-(OCH_2CH_2)_n-O-(CH_2)_{2-5}-\overset{O}{C}-CH_3$ | $H_3C-(OCH_2CH_2)_n-O-(CH_2)_{2-5}-\overset{NH-(EPO)}{\underset{CH_3}{C}}$ secondary amine linkage (to a secondary carbon) |

TABLE 1-continued

Amine-Specific Polymeric Reagents and the EPO Moiety Conjugate Formed Therefrom

| Polymeric Reagent | Corresponding Conjugate |
|---|---|
| H₃CO—(CH₂CH₂O)ₙ—CH₂—S(=O)₂—CH₂—CF₃<br><br>mPEG Tresylate Reagent | H₃CO—(CH₂CH₂O)ₙ—CH₂CH₂—NH—(EPO)<br><br>Secondary Amine Linkage |
| H₃C—(OCH₂CH₂)ₙ—O—CH₂CH₂—(maleimide)<br><br>mPEG Maleimide Reagent<br>(under certain reaction conditions such as pH > 8) | H₃C—(OCH₂CH₂)ₙ—O—CH₂CH₂—(succinimide-NH—(EPO))<br><br>Secondary Amine Linkage |
| H₃C—(OCH₂CH₂)ₙ—O—CH₂CH₂—NH—C(=O)—CH₂CH₂—(maleimide)<br><br>mPEG Maleimide Reagent<br>(under certain reaction conditions such as pH > 8) | H₃C—(OCH₂CH₂)ₙ—O—CH₂CH₂—NH—C(=O)—CH₂CH₂—N(succinimide)—NH—(EPO)<br><br>Secondary Amine Linkage |
| H₃C—(OCH₂CH₂)ₙ—O—CH₂CH₂—C(=O)—NH—CH₂CH₂—NH—C(=O)—CH₂CH₂—(maleimide)<br><br>mPEG Maleimide Reagent<br>(under certain reaction conditions such as pH > 8) | H₃C—(OCH₂CH₂)ₙ—O—CH₂CH₂—C(=O)—NH—CH₂CH₂—NH—C(=O)—CH₂CH₂—N(succinimide)—NH—(EPO)<br><br>Secondary Amine Linkage |

TABLE 1-continued

Amine-Specific Polymeric Reagents and the EPO Moiety Conjugate Formed Therefrom

| Polymeric Reagent | Corresponding Conjugate |
|---|---|
| mPEG Forked Maleimide Reagent (under certain reaction conditions such as pH > 8) | Secondary Amine Linkages |
| Branched mPEG2 Maleimide Reagent (under certain reaction conditions such as pH > 8) | Secondary Amine Linkage |

TABLE 1-continued

Amine-Specific Polymeric Reagents and the EPO Moiety Conjugate Formed Therefrom

| Polymeric Reagent | Corresponding Conjugate |
|---|---|
| Biotin-(CH$_2$)$_4$—NH—CH$_2$CH$_2$—(OCH$_2$CH$_2$)$_n$—OCH$_2$CH$_2$C(=O)—O—N-succinimidyl<br><br>Heterobifunctional PEG-Succinimidyl Reagent | Biotin-(CH$_2$)$_4$—NH—CH$_2$CH$_2$—(OCH$_2$CH$_2$)$_n$—OCH$_2$CH$_2$C(=O)—NH—EPO<br><br>Amide Linkage |
| H$_3$C—(OCH$_2$CH$_2$)$_n$—O—C(=O)—NH—CH$_2$—CH$_2$—CH$_2$—CH$_2$—CH(—C(=O)—NH—CH$_2$CH(=O))—NH—C(=O)—O—(CH$_2$CH$_2$O)$_n$—CH$_3$<br><br>Branched mPEG2-Aldehyde Reagent | H$_3$C—(OCH$_2$CH$_2$)$_n$—O—C(=O)—NH—CH$_2$—CH$_2$—CH$_2$—CH$_2$—CH(—C(=O)—NH—CH$_2$CH$_2$—NH—EPO)—NH—C(=O)—O—(CH$_2$CH$_2$O)$_n$—CH$_3$<br><br>Secondary Amine Linkage |

Conjugation of a polymeric reagent to an amino group of an EPO moiety can be accomplished by one of ordinary skill in the art without undue experimentation. In one approach, an EPO moiety is conjugated to an activated polymeric reagent comprising at least one leaving group, e.g., a succinimidyl derivative such as N-hydroxysuccinimide (NHS) or any other suitable leaving group. For example, the polymer reagent bearing an NHS or other leaving group is reacted with the EPO moiety, typically in aqueous media, at a pH of about 5.5 to 8.5. The reaction is typically carried out in a non-amine containing buffer such as phosphate buffer (e.g., sodium or potassium phosphate), HEPES, MES, PBS, MES, or sodium acetate. Reaction times will vary depending upon reaction temperature, although reactions are typically complete in from about 0.5 hours to about 48 hours. Typically, the coupling reaction is carried out at temperatures ranging from about −10° C. to about 40° C., and result in the covalent attachment of the polymer to the EPO moiety.

Depending upon the particular reactivity of the polymeric reagent employed, the polymeric reagent is combined with EPO at one of the following stoichiometries: 0.5:1 molar ratio of polymeric reagent to EPO moiety per se or greater, 1:1 or greater, 2:1 or greater, 3:1 or greater, 4:1 or greater, 5:1 or greater, 10:1 or greater, 15:1 or greater, 20:1 or greater, and 25:1 or greater.

As described above, in one or more embodiments of the method, the conjugation reaction is modified by using a pH-reversible amino-protective agent such as a cyclic dicarboxylic acid anhydride. In the method, prior to reaction with an activated polymeric reagent, the EPO moiety is mixed with the amino-protective agent, e.g., a maleic or citraconylic anhydride, which partially reacts with the most reactive amino sites in EPO to form an amino-protected EPO moiety. This amino-protected EPO moiety is then reacted with the activated polymeric reagent under conditions effective to provide a polymer-amino-protected EPO moiety conjugate, which is then deprotected (e.g., by altering the pH) to provide the desired polymer-EPO moiety conjugate, preferably wherein the resulting EPO-conjugate composition contains a minority of conjugate species having polymer covalently attached at lysine 52. Even more preferably, in one or more embodiments, the resulting conjugate composition additionally contains a minority of conjugate species having polymer covalently attached to the N-terminus of the EPO-moiety. One preferred maleic anhydride is dimethylmaleic anhydride (Tsunoda, S., et al., *J of Pharmacology and Experimental Therapeutics*, 1999, 290 (1), 368-372).

In addition, an amide linkage can similarly be formed by reacting an amine-terminated non-peptidic water-soluble polymer with an EPO moiety bearing an activating a carboxylic acid group.

Typical of another approach useful for conjugating the EPO moiety to a polymeric reagent is reductive amination to conjugate a primary amine of an EPO moiety to a polymeric reagent functionalized with a ketone, aldehyde or hydrated forms thereof (e.g., ketone hydrate, aldehyde hydrate). In this approach, the primary amine from the EPO moiety reacts with the carbonyl group of the aldehyde or ketone (or the corresponding hydroxyl-containing group of a hydrated aldehyde or ketone), thereby forming a Schiff base. The Schiff base, in turn, is then reduced to a stable conjugate through use of a reducing agent such as sodium borohydride or sodium cyanoborohydride. Selective reactions (e.g., at the N-terminus) are possible, particularly with a polymer functionalized with a ketone or an alpha-methyl branched aldehyde and/or under specific reaction conditions (e.g., reduced pH).

Preferred amine groups in EPO that can serve as a site for attaching a polymer include those amine groups found within a lysine residue. In addition, the N-terminus of any EPO moiety that is a protein can serve as a polymeric attachment site.

Carboxyl groups represent another functional group that can serve as a point of attachment on the EPO moiety. Structurally, the conjugate will comprise the following:

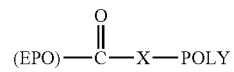

where (EPO) and the adjacent carbonyl group corresponds to the carboxyl-containing EPO moiety residue, X is a linkage, preferably a heteroatom selected from O, —NH, and S, and POLY is a water-soluble polymer such as PEG, optionally terminating in an end-capping moiety.

The —C(O)—X linkage results from the reaction between a polymeric derivative bearing a terminal functional group and a carboxyl-containing EPO moiety. As discussed above, the specific linkage will depend on the type of functional group utilized. If the polymer is end-functionalized or "activated" with a hydroxyl group, or an activated ester or the like, the resulting linkage will be a carboxylic acid ester and X will be O. If the polymer backbone is functionalized with a thiol group, the resulting linkage will be a thioester and X will be S. When certain multi-arm, branched or forked polymers are employed, the C(O)X moiety, and in particular the X moiety, may be relatively more complex and may include a longer linkage structure.

Water-soluble derivatives containing a hydrazide moiety are also useful for conjugation at carboxyl groups as illustrated by the reagents and corresponding conjugates in the following table. In the tables herein, "(EPO)" and "EPO" are used interchangeably and refer to the EPO moiety following conjugation.

TABLE 2

Carboxyl-Specific Polymeric Reagents and the EPO Moiety Conjugate Formed Therefrom

| Polymeric Reagent | Corresponding Conjugate |
|---|---|
| H₃CO—(CH₂CH₂O)ₙCH₂CH₂—C(=O)—NH—NH₂<br>mPEG-Hydrazine Reagent | H₃CO—(CH₂CH₂O)ₙCH₂CH₂—C(=O)—NH—N=C—EPO<br>Hydrazone Linkage |

TABLE 2-continued

Carboxyl-Specific Polymeric Reagents and the EPO Moiety Conjugate Formed Therefrom

| Polymeric Reagent | Corresponding Conjugate |
|---|---|
| H$_3$CO—(CH$_2$CH$_2$O)$_n$CH$_2$CH$_2$—O—CH$_2$—C(=O)—NH—NH$_2$<br>mPEG-Hydrazine Reagent | H$_3$CO—(CH$_2$CH$_2$O)$_n$CH$_2$CH$_2$—O—CH$_2$—C(=O)—NH—N=C—EPO<br>Hydrazone Linkage |
| H$_3$CO—(CH$_2$CH$_2$O)$_n$CH$_2$CH$_2$—NH—C(=O)—NH—NH$_2$<br>mPEG-Hydrazine Reagent | H$_3$CO—(CH$_2$CH$_2$O)$_n$CH$_2$CH$_2$—NH—C(=O)—NH—N=C—EPO<br>Hydrazone Linkage |
| H$_3$CO—(CH$_2$CH$_2$O)$_n$CH$_2$CH$_2$—NH—NH—C(=O)—NH—NH$_2$<br>mPEG-Hydrazine Reagent | H$_3$CO—(CH$_2$CH$_2$O)$_n$CH$_2$CH$_2$—NH—NH—C(=O)—NH—N=C—EPO<br>Hydrazone Linkage |
| H$_3$CO—(CH$_2$CH$_2$O)$_n$CH$_2$CH$_2$—NH—C(=S)—NH—NH$_2$<br>mPEG-Hydrazine Reagent | H$_3$CO—(CH$_2$CH$_2$O)$_n$CH$_2$CH$_2$—NH—C(=S)—NH—N=C—EPO<br>Hydrazone Linkage |
| H$_3$CO—(CH$_2$CH$_2$O)$_n$CH$_2$CH$_2$—NH—NH—C(=S)—NH—NH$_2$<br>mPEG-Hydrazine Reagent | H$_3$CO—(CH$_2$CH$_2$O)$_n$CH$_2$CH$_2$—NH—NH—C(=S)—NH—N=C—EPO<br>Hydrazone Linkage |
| H$_3$CO-(CH$_2$CH$_2$O)$_n$CH$_2$CH$_2$—NH—C(=O)—NH—NH—C(=O)—NH—NH$_2$<br>mPEG-Hydrazine Reagent | H$_3$CO-(CH$_2$CH$_2$O)$_n$CH$_2$CH$_2$—NH—C(=O)—NH—NH—C(=O)—NH—N=C-EPO<br>Hydrazone Linkage |
| H$_3$CO—(CH$_2$CH$_2$O)$_n$CH$_2$CH$_2$—O—C(=O)—NH—NH$_2$<br>mPEG-Hydrazine Reagent | H$_3$CO—(CH$_2$CH$_2$O)$_n$CH$_2$CH$_2$—O—C(=O)—NH—N=C—EPO<br>Hydrazone Linkage |

Thiol groups contained within the EPO moiety can serve as effective sites of attachment for the water-soluble polymer. In particular, cysteine residues provide thiol groups when the EPO moiety is a protein. The thiol groups in such cysteine residues can then reacted with an activated PEG that is specific for reaction with thiol groups, e.g., an N-maleimidyl polymer or other derivative, as described in U.S. Pat. No. 5,739,208 and in International Patent Publication No. WO 01/62827.

With respect to both SEQ ID NO: 1 and SEQ ID NO: 2, there are four thiol-containing cysteine residues. Thus, preferred thiol attachment sites are associated with cysteine residues at any position 7, 29, 33, and 161. To the extent that each of the cysteine residues within EPO participate in disulfide bonding, it is preferred not to disrupt such bonds as disruption of the tertiary structure of the EPO moiety might occur and result in potentially significantly decreased EPO activity. Thus, to the extent that any particular EPO moiety lacks a thiol group or disruption of disulfide bonds is to be avoided, it is possible to add a cysteine residue to the EPO moiety using conventional synthetic techniques. See, for example, WO 90/12874. In addition, conventional genetic engineering processes can also be used to introduce a cysteine residue into the EPO moiety. In some embodiments, however, it is preferred not to introduce and additional cysteine residue and/or thiol group.

Specific examples, along with the corresponding conjugate, are provided in Table 3, below. In the table, the variable (n) represents the number of repeating monomeric units and "—S-(EPO)" represents the EPO moiety residue following conjugation to the water-soluble polymer. While each polymeric portion [e.g., (OCH$_2$CH$_2$)$_n$ or (CH$_2$CH$_2$O)$_n$] presented in Table 3 terminates in a "CH$_3$" group, other groups (such as H and benzyl) can be substituted therefor.

TABLE 3
Thiol-Specific Polymeric Reagents and the EPO Moiety Conjugate Formed Therefrom
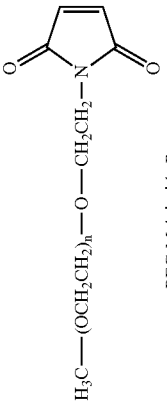

TABLE 3-continued

Thiol-Specific Polymeric Reagents and the EPO Moiety Conjugate Formed Therefrom

| Polymeric Reagent | Corresponding Conjugate |
| --- | --- |
| mPEG Maleimide Reagent | Thioether Linkage |
| mPEG Forked Maleimide Reagent | Thioether Linkage |
| Branched mPEG2 Maleimide Reagent | Thioether Linkage |

TABLE 3-continued

Thiol-Specific Polymeric Reagents and the EPO Moiety Conjugate Formed Therefrom

TABLE 3-continued

Thiol-Specific Polymeric Reagents and the EPO Moiety Conjugate Formed Therefrom

| Polymeric Reagent | Corresponding Conjugate |
|---|---|
| $H_3C-(OCH_2CH_2)_n-O-CH_2CH_2-S(=O)_2-CH=CH_2$<br>mPEG Vinyl Sulfone Reagent | $H_3C-(OCH_2CH_2)_n-O-CH_2CH_2-S(=O)_2-CH_2-CH_2-S-(EPO)$<br>Thioether Linkage |
| $H_3C-(OCH_2CH_2)_n-O-CH_2CH_2-C(=O)-NH-CH_2-CH_2-SH$<br>mPEG Thiol Reagent | $H_3C-(OCH_2CH_2)_n-O-CH_2CH_2-C(=O)-NH-CH_2-CH_2-S-S-(EPO)$<br>Disulfide Linkage |
| $HS-CH_2CH_2-NH-C(=O)-CH_2CH_2-(OCH_2CH_2)_n-C(=O)-NH-CH_2-CH_2-SH$<br>Homobifunctional PEG Thiol Reagent | $(EPO)-S-S-CH_2CH_2-NH-C(=O)-CH_2CH_2-(OCH_2CH_2)_n-C(=O)-NH-CH_2-CH_2-S-S-(EPO)$<br>Disulfide Linkages |
| $H_3CO-(CH_2CH_2O)_n-CH_2CH_2CH_2-S-S-\text{(2-pyridyl)}$<br>mPEG Disulfide Reagent | $H_3CO-(CH_2CH_2O)_n-CH_2CH_2CH_2-S-S-(EPO)$<br>Disulfide Linkage |
| $\text{(2-pyridyl)}-S-S-CH_2CH_2-(CH_2CH_2O)_n-CH_2CH_2CH_2-S-S-\text{(2-pyridyl)}$<br>Homobifunctional Disulfide Reagent | $(EPO)-S-S-CH_2CH_2-(CH_2CH_2O)_n-CH_2CH_2CH_2-S-S-(EPO)$<br>Disulfide Linkages |

With respect to conjugates formed from water-soluble polymers bearing one or more maleimide functional groups (regardless of whether the maleimide reacts with an amine or thiol group on the EPO moiety), the corresponding maleamic acid form(s) of the water-soluble polymer can also react with the EPO moiety. Under certain conditions (e.g., a pH of about 7-9 and in the presence of water), the maleimide ring will "open" to form the corresponding maleamic acid. The maleamic acid, in turn, can react with an amine or thiol group of an EPO moiety. Exemplary maleamic acid-based reactions are schematically shown below. POLY represents the water-soluble polymer, and (EPO) represents the EPO moiety.

located between the EPO moiety and the polymer. With respect to the indirect attachment, the one or more atoms is conventionally referred to as a "spacer moiety," or as a "linking moiety or linking group" which can include one or more of carbon atoms, nitrogen atoms, sulfur atoms, oxygen atoms, and combinations thereof. A spacer moiety may also be interposed, e.g., between a water-soluble polymer and a terminal portion of the overall polymer reagent structure, wherein the terminal portion is typically where covalent attachment to EPO occurs. The spacer moiety can comprise an amide, secondary amine, carbamate, thioether, or disulfide group. Non-limiting examples of specific spacer moieties include those

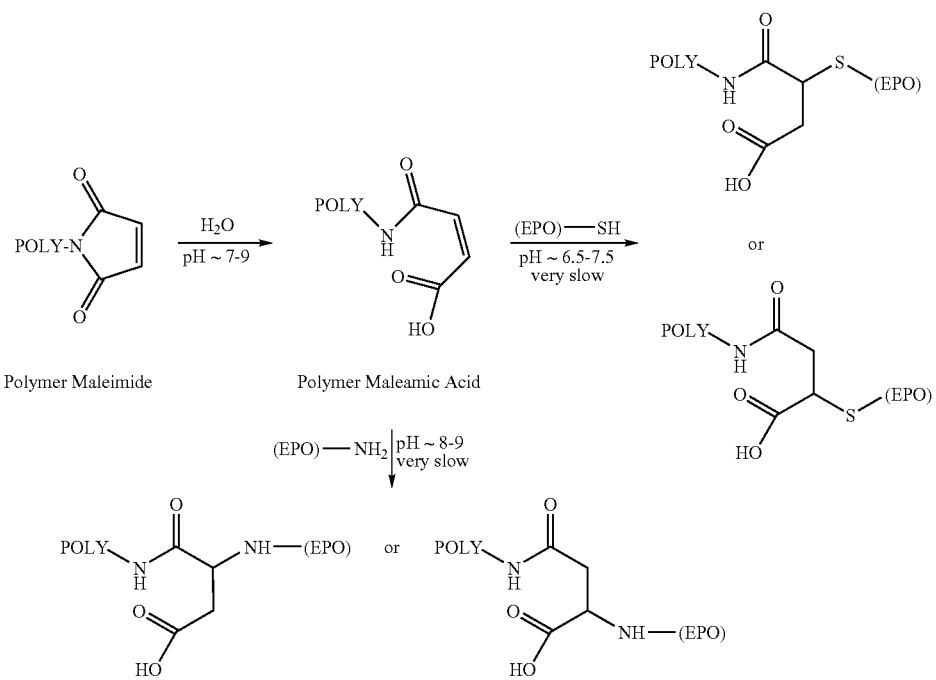

A representative conjugate in accordance with the invention can have the following structure:

POLY-L$_{0,1}$—C(O)Z—Y—S—S-(EPO)

wherein POLY is a water-soluble polymer, L is an optional linker, Z is a heteroatom selected from the group consisting of O, NH, and S, and Y is selected from the group consisting of C$_{2-10}$ alkyl, C$_{2-10}$ substituted alkyl, aryl, and substituted aryl, and (EPO) is an EPO moiety. Polymeric reagents that can be reacted with an EPO moiety and result in this type of conjugate are described in U.S. Patent Application Publication No. 2005/0014903.

Preferred thiol groups in an EPO moiety that can serve as a site for attaching a polymeric reagent include those thiol groups found within cysteine residues.

With respect to polymeric reagents, those described here and elsewhere can be purchased from commercial sources (e.g., Nektar Therapeutics, Huntsville Ala.). In addition, methods for preparing the polymeric reagents are described in the literature.

The attachment between the EPO moiety and the non-peptidic water-soluble polymer can be direct, wherein no intervening atoms are located between the EPO moiety and the polymer, or indirect, wherein one or more atoms are selected from the group consisting of —O—, —S—, —S—S—, —C(O)—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—CH$_2$—CH$_2$—, —CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—

—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, —CH$_2$—CH$_2$—CH$_2$—C(O)—NH—CH$_2$—CH$_2$—NH—C(O)—CH$_2$—CH$_2$—, —O—C(O)—NH—[CH$_2$]$_h$—(OCH$_2$CH$_2$)$_j$—, bivalent cycloalkyl group, —O—, —S—, an amino acid, —N(R$^6$)—, and combinations of two or more of any of the foregoing, wherein R$^6$ is H or an organic radical selected from the group consisting of alkyl, substituted alkyl, alkenyl, substituted alkenyl, alkynyl, substituted alkynyl, aryl and substituted aryl, (h) is zero to six, and (j) is zero to 20. Other specific spacer moieties have the following structures: —C(O)—NH—(CH$_2$)$_{1-6}$—NH—C(O)—, —NH—C(O)—NH—(CH$_2$)$_{1-6}$—NH—C(O)—, and —O—C(O)—NH—(CH$_2$)$_{1-6}$—NH—C(O)—, wherein the subscript values following each methylene indicate the number of methylenes contained in the structure, e.g., (CH$_2$)$_{1-6}$ means that the structure can contain 1, 2, 3, 4, 5 or 6 methylenes. Additionally, any of the above spacer moieties may further include an ethylene oxide oligomer chain comprising 1 to 20 ethylene oxide monomer units [i.e., —(CH$_2$CH$_2$O)$_{1-20}$]. That is, the ethylene oxide oligomer chain can occur before or after the spacer moiety, and optionally in between any two atoms of a spacer moiety comprised of two or more atoms. Also, the oligomer chain would not be considered part of the spacer moiety if the oligomer is adjacent to a polymer segment and merely represent an extension of the polymer segment.

Additional examplary EPO polymer conjugates and polymer reagents in accordance with one or more embodiments of the invention are provided below, and are additionally described in the Examples which follow.

One exemplary conjugate of erythropoietin (EPO) possesses the structure:

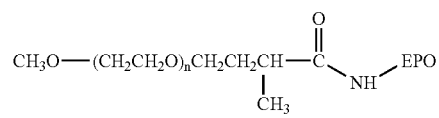

wherein POLY is a polyalkylene oxide, Q is an optional linking group having a length of from one to 10 atoms, m is an integer ranging from 0 to 20, Z is selected from the group consisting of alkyl, substituted alkyl, aryl and substituted aryl, EPO is a residue of erythropoietin, and "—NH-EPO" represents an amino group of EPO.

In reference to the structure above, Z refers to a substituent on the carbon alpha to the carbonyl group. The placement of the substituent in the α-position provides additional selectivity to the reagent, and thus, in the resulting conjugate. Preferably, Z is lower alkyl or substituted lower alkyl, e.g., methyl, ethyl, n-propyl, isopropyl, n-butyl, or isobutyl. Most preferably, Z is methyl.

An illustrative EPO conjugate structure falling within the generalized structure provided above comprises:

$$CH_3O-(CH_2CH_2O)_nCH_2CH_2CH-\underset{\underset{CH_3}{|}}{C}\underset{NH}{\overset{O}{\|}}\diagdown EPO$$

where n typically ranges from about 200 to about 1400.

Also provided in one or more embodiments of the invention are EPO conjugates corresponding to one or more of the following structures:

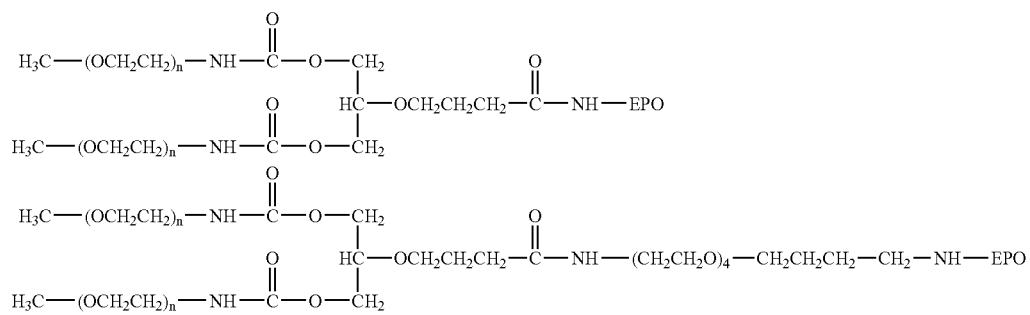

where n corresponds to the values previously described and EPO is a residue of an EPO moiety.

Compositions

The conjugates typically form part of a composition. Generally, the composition comprises a plurality of conjugates, preferably although not necessarily, each conjugate is comprised of the same EPO moiety (i.e., within the entire composition, only one type of EPO moiety is found). In addition, the composition can comprise a plurality of conjugates wherein any given conjugate is comprised of a moiety selected from the group consisting of two or more different EPO moieties (i.e., within the entire composition, two or more different EPO moieties are found). Optimally, however, substantially all of the plurality of conjugates in the composition (e.g., 85% or more of the plurality of conjugates in the composition) are each comprised of the same EPO moiety.

The composition can comprise a single conjugate species (e.g., a monoPEGylated conjugate wherein a single polymer is attached at the same location or position on EPO for substantially all conjugates in the composition) or a mixture of conjugate species (e.g., a mixture of monoPEGylated conjugates where attachment of the polymer occurs at different sites and/or a mixture of monoPEGylated, diPEGylated and triPEGylated, etc., conjugates). The compositions can also comprise other conjugates having four, five, six, seven, eight or more polymers attached to any given moiety having EPO activity. In addition, the invention includes instances wherein the composition comprises a plurality of conjugates, each conjugate comprising one non-peptidic water-soluble polymer covalently attached to one EPO moiety, as well as compositions comprising two, three, four, five, six, seven, eight, or more water-soluble polymers covalently attached to one EPO moiety.

In one or more embodiments, it is preferred that the conjugate-containing composition is free or substantially free of albumin. It is also preferred that the composition is free or substantially free of proteins that do not have EPO activity. Thus, it is preferred that the composition is 85%, more preferably 95%, and most preferably 99% free of albumin. Additionally, it is preferred that the composition is 85%, more preferably 95%, and most preferably 99% free of any protein that does not have EPO activity.

Control of the desired number of polymers for any given moiety can be achieved by selecting the proper polymeric reagent, the ratio of polymeric reagent to the EPO moiety, temperature, pH conditions, and other aspects of the conjugation reaction. In addition, reduction or elimination of the undesired conjugates (e.g., those conjugates having four or more attached polymers) can be achieved through purification.

For example, the polymer-EPO moiety conjugates can be purified to obtain/isolate different conjugated species. Specifically, the product mixture can be purified to obtain an average of anywhere from one, two, three, four, five or more PEGs per EPO moiety, typically one, two or three PEGs per EPO moiety. The strategy for purification of the final conjugate reaction mixture will depend upon a number of factors, including, for example, the molecular weight of the polymeric reagent employed, the particular EPO moiety, the desired dosing regimen, and the residual activity and in vivo properties of the individual conjugate(s).

Exemplary compositions in accordance with the invention are those comprising monoPEGylated EPO, diPEGylated EPO, or mixtures thereof. Illustrative compositions include the following: an EPO conjugate composition wherein greater than about 85% of the PEG-EPO conjugates are monoPEGylated EPO, or an EPO conjugate composition wherein greater than about 90%, or even about 95% or greater of the PEG-EPO conjugates are monoPEGylated EPO.

If desired, conjugates having different molecular weights can be isolated using gel filtration chromatography and/or ion exchange chromatography. That is to say, gel filtration chromatography is used to fractionate differently numbered polymer-to-EPO moiety ratios (e.g., 1-mer, 2-mer, 3-mer, and so forth, wherein "1-mer" indicates 1 polymer to EPO moiety, "2-mer" indicates two polymers to EPO moiety, and so on) on the basis of their differing molecular weights (where the difference corresponds essentially to the average molecular weight of the water-soluble polymer portion). For example, in an exemplary reaction where a 35,000 Dalton protein is randomly conjugated to a polymeric reagent having a molecular weight of about 20,000 Daltons, the resulting reaction mixture may contain unmodified protein (having a molecular weight of about 35,000 Daltons), monoPEGylated protein (having a molecular weight of about 55,000 Daltons), diPEGylated protein (having a molecular weight of about 75,000 Daltons), and so forth.

While this approach can be used to separate PEG and other polymer-EPO moiety conjugates having different molecular weights, this approach is generally ineffective for separating positional isoforms having different polymer attachment sites within the EPO moiety. For example, gel filtration chromatography can be used to separate from each other mixtures of PEG 1-mers, 2-mers, 3-mers, and so forth, although each of the recovered conjugate compositions may contain PEG(s) attached to different reactive groups (e.g., lysine residues) within the EPO moiety.

Gel filtration columns suitable for carrying out this type of separation include Superdex™ and Sephadex™ columns available from Amersham Biosciences (Piscataway, N.J.). Selection of a particular column will depend upon the desired fractionation range desired. Elution is generally carried out using a suitable buffer, such as phosphate, acetate, or the like. The collected fractions may be analyzed by a number of different methods, for example, (i) absorbance at 280 nm for protein content, (ii) dye-based protein analysis using bovine serum albumin (BSA) as a standard, (iii) iodine testing for PEG content (Sims et al. (1980) *Anal. Biochem*, 107:60-63), (iv) sodium dodecyl sulfate polyacrylamide gel electrophoresis (SDS PAGE), followed by staining with barium iodide, and (v) high performance liquid chromatography (HPLC).

Separation of positional isoforms is carried out by reverse phase-high performance liquid chromatography (RP-HPLC) using a suitable column (e.g., a C18 column or C3 column, available commercially from companies such as Amersham Biosciences or Vydac) or by ion exchange chromatography using an ion exchange column, e.g., a Sepharose™ ion exchange column available from Amersham Biosciences. Either approach can be used to separate polymer-EPO isomers having the same molecular weight (i.e., positional isoforms).

The compositions are preferably substantially free of proteins that do not have EPO activity. In addition, the compositions preferably are substantially free of all other noncovalently attached water-soluble polymers. In some circumstances, however, the composition can contain a mixture of polymer-EPO moiety conjugates and unconjugated EPO moiety.

Optionally, the composition of the invention further comprises a pharmaceutically acceptable excipient. If desired, the pharmaceutically acceptable excipient can be added to a conjugate to form such a composition.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The composition can also include an antimicrobial agent for preventing or deterring microbial growth. Nonlimiting examples of antimicrobial agents suitable for one or more embodiments of the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the composition as well. Antioxidants are used to prevent oxidation, thereby preventing the deterioration of the conjugate or other components of the preparation. Suitable antioxidants for use in one or more embodiments of the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate (i.e., the conjugate formed between the active agent and the polymeric reagent) in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint. Typically, a pharmaceutical composition of the invention will contain different amounts of an EPO moiety, e.g., from about 10 to about 10,000 µg/ml EPO conjugate, preferably from about 50 µg/ml to about 400 µg/ml EPO conjugate.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5% to about 98% by weight, more preferably from about 15 to about 95% by weight of the excipient, with concentrations less than 30% by weight most preferred.

These foregoing pharmaceutical excipients along with other excipients are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The compositions encompass all types of formulations and in particular those that are suited for injection, e.g., powders or lyophilates that can be reconstituted as well as liquids. Examples of suitable diluents for reconstituting solid compositions prior to injection include bacteriostatic water for injection, dextrose 5% in water, phosphate-buffered saline, Ringer's solution, saline, sterile water, deionized water, and combinations thereof. With respect to liquid pharmaceutical compositions, solutions and suspensions are envisioned.

The compositions of one or more embodiments of the present invention are typically, although not necessarily, administered via injection and are therefore generally liquid solutions or suspensions immediately prior to administration. The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intra-arterial, and so forth.

Administration

The invention also provides a method for administering a conjugate as provided herein to a patient suffering from a condition that is responsive to treatment with the conjugate. The method comprises administering, generally via injection, a therapeutically effective amount of the conjugate (preferably provided as part of a pharmaceutical composition). As previously described, the conjugates can be administered parenterally by intravenous injection, or less preferably by intramuscular or by subcutaneous injection. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

The method of administering may be used to treat any condition that can be remedied or prevented by administration of the conjugate. Those of ordinary skill in the art appreciate which conditions a specific conjugate can effectively treat. For example, an EPO conjugate of the invention can be used to treat patients suffering from anemia. Exemplary anemies include (a) anemia associated with chronic renal failure, (b) anemia related to zidovudine therapy in HIV-infected patients, and (c) anemia in cancer patients undergoing chemotherapy. In addition, the conjugates can be used to reduce allgeneic blood transfusion in surgery patients. Advantageously, the conjugate can be administered to the patient prior to, simultaneously with, or after administration of another active agent, such as a chemotherapy agent. In addition, the conjugate can be administered to an anemic patient prior to undergoing surgery.

The actual dose to be administered will vary depending upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day. For example, a conjugate of the invention may be administered at 0.01 to 10 μg per kilogram body weight, preferably 0.1 to 3 μg per kilogram body weight, e.g., once daily, every other day, twice weekly, once weekly, once every other week, or as described below.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted. Particularly preferred compositions are those that are dosed at a frequency of about once a week or less. As seen in the accompanying Examples, a preferred EPO conjugate, mono-mPEG-SMB-30 kD-EPO, was shown in vivo to sustain higher blood levels over an extended period of time than either the unmodified EPO control, or a currently marketed version of EPO.

One advantage of administering certain conjugates described herein is that individual water-soluble polymer portions can be cleaved. Such a result is advantageous when clearance from the body is potentially a problem because of the polymer size. Optimally, cleavage of each water-soluble polymer portion is facilitated through the use of physiologically cleavable and/or enzymatically degradable linkages such as amide, carbonate or ester-containing linkages. In this way, clearance of the conjugate (via cleavage of individual water-soluble polymer portions) can be modulated by selecting the polymer molecular size and the type functional group that would provide the desired clearance properties. One of ordinary skill in the art can determine the proper molecular size of the polymer as well as the cleavable functional group. For example, one of ordinary skill in the art, using routine experimentation, can determine a proper molecular size and cleavable functional group by first preparing a variety of polymer derivatives with different polymer weights and cleavable functional groups, and then obtaining the clearance profile (e.g., through periodic blood or urine sampling) by administering the polymer derivative to a patient and taking periodic blood and/or urine sampling. Once a series of clearance profiles have been obtained for each tested conjugate, a suitable conjugate can be identified.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All articles, books, patents and other publications referenced herein are hereby incorporated by reference in their entireties.

EXPERIMENTAL

The practice of the invention will employ, unless otherwise indicated, conventional techniques of organic synthesis, bio-chemistry, protein purification and the like, which are within the skill of the art. Such techniques are fully explained in the literature. See, for example, J. March, Advanced Organic Chemistry: Reactions Mechanisms and Structure, 4th Ed. (New York: Wiley-Interscience, 1992), supra. Reagents and materials are commercially available unless specifically stated to the contrary.

In the following examples, efforts have been made to ensure accuracy with respect to numbers used (e.g., amounts, temperatures, etc.) but some experimental error and deviation should be accounted for. Unless indicated otherwise, temperature is in degrees C. and pressure is at or near atmospheric pressure at sea level. Each of the following examples is considered to be instructive to one of ordinary skill in the art for carrying out one or more of the embodiments described herein.

Although other abbreviations known by one having ordinary skill in the art will be referenced, other reagents and materials will be used, and other methods known by one having ordinary skill in the art will be used, the following list and methods description is provided for the sake of convenience.

| ABBREVIATIONS: | |
|---|---|
| mPEG-SPA | mPEG-succinimidyl propionate |
| mPEG-SBA | mPEG-succinimidyl butanoate |
| mPEG-MAL | mPEG-maleimide, $CH_3O-(CH_2CH_2O)_n-CH_2CH_2$-MAL |
| mPEG-SMP | mPEG-succinimidyl α-methylpropanoate, $CH_3O-(CH_2CH_2O)_n-CH_2-CH(CH_3)-C(O)-O$-succinimide |
| mPEG-SMB | mPEG-succinimidyl α-methylbutanoate, $CH_3O-(CH_2CH_2O)_n-CH_2CH_2-CH(CH_3)-C(O)-O$-succinimide |
| anh. | Anhydrous |
| Fmoc | 9-fluorenylmethoxycarbonyl |
| $NaCNBH_3$ | sodium cyanoborohydride |
| HCl | hydrochloric acid |
| NMR | nuclear magnetic resonance |
| DI | deionized |
| MW | molecular weight |
| K or kDa | kilodaltons |
| IEX | ion exchange |
| SEC | Size exclusion chromatography |
| HPLC | high performance liquid chromatography |
| FPLC | fast protein liquid chromatography |
| SDS-PAGE | sodium dodecyl sulfate-polyacrylamide gel electrophoresis |
| MALDI-TOF | Matrix Assisted Laser Desorption Ionization, Time-of-Flight |
| TLC | Thin Layer Chromatography |

EPO corresponding to the amino acid sequence of SEQ. ID. NO. 1. was used in Examples 1-10. The EPO stock solution contained about 0.5 mg/mL to 2.1 mg/mL of EPO (depending on the lot) in an amine-free buffer. Polymeric reagents are available from Nektar Therapeutics, Huntsville, Ala., unless indicated otherwise.

Sample Analysis

Samples were analyzed by RP-HPLC (Reverse Phase) and purified using IEX (Ion Exchange) chromatography. RP-HPLC was also used to prepare standard curves to evaluate protein and conjugate concentrations in various preparations. The Bradford Protein Assay (Bradford, MM. *Analytical Biochemistry* 72: 248-254, 1976) can also be used to determine protein content.

SDS-PAGE Analysis

Certain samples as indicated were analyzed using SDS-PAGE for sample detection only. Samples were analyzed by sodium dodecyl sulfate-polyacrylamide gel electrophoresis (SDS-PAGE) using Sure-Lock II (Invitrogen). Samples were mixed with sample buffer. Then, the prepared samples were loaded onto a gel and run for approximately 30 minutes.

Example 1

Random PEGylation of EPO with mPEG-SMB, 30 kDa

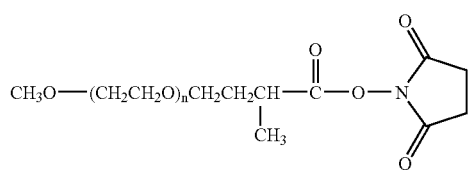

mPEG-SMB, 30 kDa mPEG-SMB, 30 kDa, stored at −20° C. under argon, was warmed to ambient temperature. The warmed mPEG-SMB (20.0 mg) was dissolved in 1.0 mL of 2 mM HCl to form an mPEG-SMB solution. The mPEG-SMB solution was added to a previously prepared EPO reaction mixture (500 μL stock EPO solution, 500 μL of 20 mM NaPO$_4$, pH 6.5) until a twenty-fold molar excess of mPEG-SMB relative to EPO was reached. After the addition of the mPEG-SMB, the pH of the reaction mixture was readjusted to 6.5 and was mixed well. To allow for coupling of the mPEG-SMB to EPO via an amide linkage, the reaction solution was stirred for six hours at room temperature and thereafter stirred for twelve hours at 3-8° C. in a cold room, thereby resulting in a conjugate solution. The reaction was quenched by addition of glycine.

The conjugate solution was purified using ion exchange chromatography (anion-strong). SDS-PAGE and RP-HPLC (C$_3$) analysis was also used for the characterization. Based upon the HPLC and SDS-PAGE results, the overall PEGylation yield was 45%, meaning that approximately 45% of the EPO was conjugated to PEG. The reaction mixture contained a mixture of PEG-mers (monoPEGylated EPO, diPEGylated EPO, etc.), as well as unreacted EPO. The mixture of PEG-mers was then resolved to provide a purified monoPEG conjugate that was substantially (>90%) monoPEGylated EPO (i.e., EPO 1-mer).

Using this same approach, other conjugates can be prepared using mPEG-SMB having other weight average molecular weights.

Example 2

Random PEGylation of EPO with Branched mPEG2-N-Hydroxysuccinimide, 40 kDa

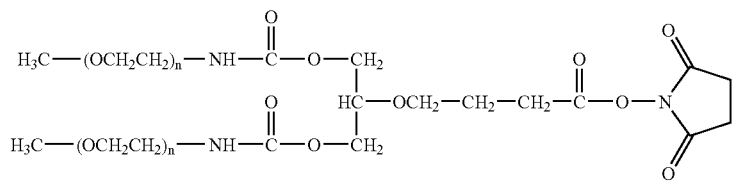

Branched mPEG2-N-Hydroxysuccinimide (NHS), 40 kDa

Branched mPEG2-N-hydroxysuccinimide, 40 kDa, stored at −20° C. under argon, was warmed to ambient temperature. The branched mPEG2-N-hydroxysuccinimide (26.7 mg) was dissolved in 1.0 mL of 2 mM HCl to form a branched mPEG2-N-hydroxy-succinimide solution. The branched mPEG2-N-hydroxysuccinimide solution was added to a previously prepared EPO reaction mixture (500 μL stock EPO solution, 500 μL of 20 mM NaPO$_4$) until a twenty-fold molar excess of branched mPEG2-N-hydroxysuccinimide solution relative to EPO was reached. After the addition of branched mPEG2-N-hydroxysuccinimide, the pH of the reaction mixture was readjusted to 6.5 and was mixed well. To allow for coupling of the branched mPEG2-N-hydroxysuccinimide to EPO via an amide linkage, the reaction solution was stirred for six hours at room temperature and thereafter stirred for twelve hours at 3-8° C. in a cold room, thereby resulting in a conjugate solution. The reaction was quenched with glycine.

The conjugate solution was purified using ion exchange chromatography (anion-strong). SDS-PAGE and RP-HPLC (C$_3$) analysis were also used for the characterization. Based upon the HPLC and SDS-PAGE results, the overall PEGylation yield was ~32%.

The reaction mixture contained a mixture of PEG-mers (monoPEGylated EPO, diPEGylated EPO, etc.), as well as unreacted EPO. The mixture of PEGmers was then resolved to provide a purified monoPEG conjugate that was substantially (>90%) monoPEGylated EPO (i.e., EPO 1-mer).

Using this same approach, other conjugates can be prepared using branched mPEG2-N-hydroxysuccinimide having other weight average molecular weights.

Example 3

Random PEGylation of EPO with mPEG-SMB, 30 kDa

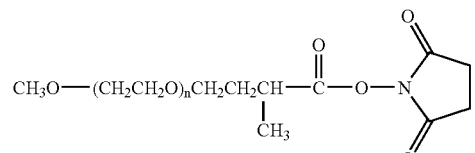

mPEG-SMB, 30 kDa mPEG-SMB, 30 kDa, stored at −20° C. under argon, was warmed to ambient temperature. Two 10.0 mg samples of the mPEG-SMB were separately dissolved in 500 μL of 2 mM HCl to form two aliquots of mPEG-SMB solution. A first aliquot of mPEG-SMB solution was added to a previously prepared EPO reaction mixture (250 µL stock EPO solution, 20 mM NaPO$_4$, pH 6.5) until a twenty-fold molar excess of mPEG-SMB relative to EPO was reached. The pH was tested and adjusted as necessary to ensure a pH of 6.5. After about thirty minutes, the second aliquot of mPEG-SMB solution was added and mixed well, thereby resulting in a reaction mixture having a forty-fold molar excess of mPEG-SMB relative to EPO. Again, the pH was tested and adjusted as necessary to ensure a pH of about 6.5. To allow for final coupling of the mPEG-SMB to EPO via an amide linkage, the reaction solution was stirred for sixteen hours at 3-8° C. in a cold room, thereby resulting in a conjugate solution. The reaction was quenched by addition of glycine.

The conjugate solution was purified using ion exchange chromatography (anion-strong). SDS-PAGE and RP-HPLC (C$_3$) analysis were also used for the characterization. Based upon the HPLC and SDS-PAGE results, the overall PEGylation yield was ~62.5% (representing about ~54% monoPEGylated and ~8.5% diPEGylated conjugates). The reaction yield was improved over that reported in Example 1 by increasing both the overall amount of PEG reagent used and the manner of its addition.

The above reaction was run again under nearly identical reaction conditions, with the exception that the pH was adjusted to approximately 7.5 after addition of each aliquot of mPEG-SMB. The resulting conjugate solution was purified using ion exchange chromatography as described above. The purified monoPEGylated product, designated 01-R-MSMBE-30, was determined by SDS-PAGE to contain approximately 94% monomer (mono-mPEG-SMB-30 kD-EPO) and 6% dimer (di-mPEG-SMB-30 kD-EPO). No triP-EGylated product was detected. The purified diPEGylated product, designated 01-R-DSMBE-30, was determined by SDS-PAGE to contain approximately 67% dimer (di-mPEG-SMB-30 kD-EPO) and 28% monomer (monomPEG-SMB-30 kD-EPO). No triPEGylated product was detected. Further separations can be carried out as desired to arrive at a composition that is substantially pure dimer.

MALDI-TOF analysis for both the mono- and diPEGylated species confirmed the covalent attachment of either one PEG moiety or two PEG moieties, respectively, to form the respective conjugate products.

Preliminary in vivo and in vitro assays were conducted on the purified conjugates, mono-mPEG-SMB-30 kD-EPO and di-mPEG-SMB-30 kD-EPO. The results are provided below. The assays confirmed the bioactivity of the subject conjugates.

TABLE 4

| Conjugate | In vivo Activity, IU/mg* | In vitro Assay** |
| --- | --- | --- |
| mono-mPEG-SMB-30kD-EPO) Sample 01-R-MSMBE-30 | 507500 | 1.9% |
| di-mPEG-SMB-30kD-EPO Sample 01-R-DSMBE-30 | 108500 | 0.9% |

*unmodified EPO possesses an activity of 120,000 IU/mg in the assay set up employed.
**for comparison, unmodified EPO is considered to possess an activity of 100%.

Using this same approach, other conjugates can be prepared using mPEG-SMB having other weight average molecular weights.

Example 4

Random PEGylation of EPO with Branched mPEG2-N-Hydroxysuccinimide, 40 kDa

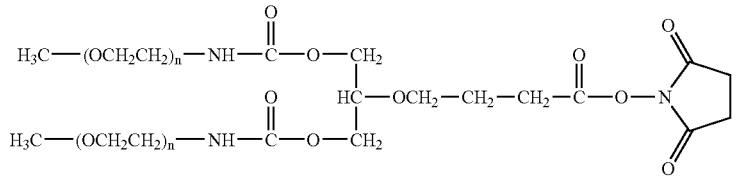

Branched mPEG2-N-Hydroxysuccinimide, 40 kDa

Branched mPEG2-N-hydroxysuccinimide, 40 kDa, stored at −20° C. under argon, was warmed to ambient temperature. Two 13.3 mg samples of the branched mPEG2-N-hydroxysuccinimide were separately dissolved in 250 µL of 2 mM HCl to form two aliquots of mPEG2-N-hydroxysuccinimide solution. A first aliquot of branched mPEG2-N-hydroxysuccinimide solution was added to a previously prepared EPO reaction mixture (250 µL stock EPO solution, 20 mM NaPO$_4$, pH 6.5) until a twent-fold molar excess of mPEG2-N-hydroxysuccinimide to EPO was reached. The pH was tested and adjusted as necessary to ensure a pH of 6.5. After about thirty minutes, the second aliquot of branched mPEG2-N-hydroxysuccinimide solution was added and mixed well, thereby resulting in a reaction mixture having forty-fold molar excess of branched mPEG2-N-hydroxysuccinimide relative to EPO. Again, the pH was tested and adjusted as necessary to ensure a pH of 6.5. To allow for final coupling of the branched mPEG2-N-hydroxysuccinimide to EPO via an amide linkage, the reaction solution was stirred for sixteen hours at 3-8° C. in a cold room, thereby resulting in a conjugate solution. The reaction was quenched by addition of glycine.

SDS-PAGE analysis was used for the characterization. Based upon the SDS-PAGE results, the PEGylation yield was ~70% (representing ~64% monoPEGylated and ~6% diPEGylated conjugates). By increasing both the amount of PEG used and the manner of its addition, the PEGylation yield was increased over that described in Example 2.

Using this same approach, other conjugates can be prepared using branched mPEG2-N-hydroxysuccinimide having other weight average molecular weights.

Example 5

Random PEGylation of EPO with mPEG-SMB, 30 kDa

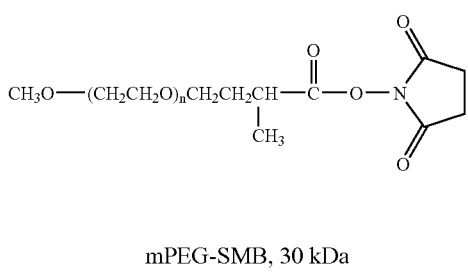

mPEG-SMB, 30 kDa

In this reaction, the hydrophobicity of the buffer system was altered by addition of ethanol.

Ethanol was added to 250 μL of a previously prepared EPO reaction mixture (250 μL stock EPO solution, 500 μL 20 mM NaPO$_4$) to form a 10% ethanol-containing EPO reaction mixture. Separately, mPEG-SMB, 30 kDa, stored at −20° C. under argon, was warmed to ambient temperature. The mPEG-SMB (13.3 mg) was dissolved in 250 μL of 2 mM HCl to form an mPEG-SMB solution. To the ethanol-containing EPO reaction mixture, the mPEG-SMB solution was added until a twenty-fold molar excess of mPEG-SMB relative to EPO was reached. The pH was tested and adjusted as necessary to ensure a pH of 6.5. After about thirty minutes, 13.3 mg of dry mPEG-SMB was added and mixed well, thereby resulting in a reaction mixture having forty-fold molar excess of mPEG-SMB relative to EPO. Again, the pH was tested and adjusted as necessary to ensure a pH of 6.5. To allow for final coupling of the mPEG-SMB to EPO via an amide linkage, the reaction solution was stirred for sixteen hours at 3-8° C. in a cold room, thereby resulting in a conjugate solution. The reaction was quenched by addition of glycine.

SDS-PAGE analysis was used for characterization of the reaction mixture. Based upon the SDS-PAGE results, the PEGylation yield was ~35% (representing ~28% monoPEGylated and ~7.0% diPEGylated conjugates).

Using this same approach, other conjugates can be prepared using mPEG-SMB having other weight average molecular weights.

Example 6

Random PEGylation of EPO with Branched mPEG2-N-Hydroxysuccinimide, 40 kDa

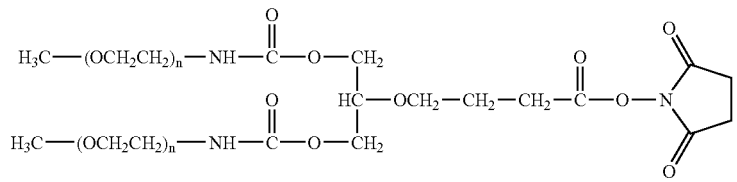

Branched mPEG2-N-Hydroxysuccinimide, 40 kDa

In this reaction, the hydrophobicity of the buffer system was altered by addition of ethanol.

Ethanol was added to 250 μL of a previously prepared EPO reaction mixture (250 μL stock EPO solution, 500 μL 20 mM NaPO$_4$) to form a 10% ethanol-containing EPO reaction mixture. Branched mPEG2-N-hydroxysuccinimide, 40 kDa, stored at −20° C. under argon, was warmed to ambient temperature. Two 13.3 mg samples of the warmed branched mPEG2-N-hydroxysuccinimide were separately dissolved in 250 μL of 2 mM HCl to form two aliquots of mPEG2-N-hydroxysuccinimide solution. A first aliquot of branched mPEG2-N-hydroxysuccinimide solution was added to the 10% ethanol-containing EPO reaction mixture until a twenty-fold molar excess of mPEG2-N-hydroxysuccinimide relative to EPO was reached. The pH was tested and adjusted as necessary to ensure a pH of 6.5. After about thirty minutes, the second aliquot of branched mPEG2-N-hydroxysuccinimide solution was added and mixed well, thereby resulting in a reaction mixture having forty-fold molar excess of branched mPEG2-N-hydroxysuccinimide relative to EPO. Again, the pH was tested and adjusted as necessary to ensure a pH of 6.5. To allow for final coupling of the branched mPEG2-N-hydroxysuccinimide to EPO via an amide linkage, the reaction solution was stirred for 16 hours at 3-8° C. in a cold room, thereby resulting in a conjugate solution. The reaction was quenched by addition of glycine.

SDS-PAGE analysis was used for characterization of the reaction mixture. Based upon the SDS-PAGE results, the PEGylation yield was ~27% (representing ~21% monoPEGylated and ~6.0% diPEGylated conjugates).

Using this same approach, other conjugates can be prepared using branched mPEG2-N-hydroxysuccinimide having other weight average molecular weights.

Example 7

Non-Random PEGylation of EPO with Branched mPEG2-N-Hydroxysuccinimide, 40 kDa

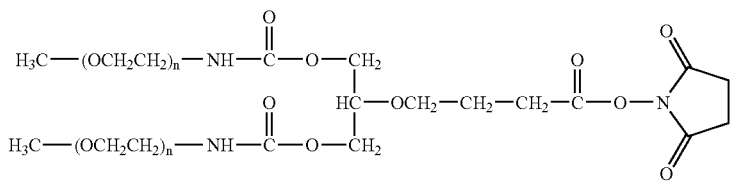

Branched mPEG2-N-Hydroxysuccinimide, 40 kDa

Prior to the conjugation reaction, 1.5 mL of reaction buffer (20 mM NaPO$_4$), pH 8.0, was added to 500 μL of stock EPO solution. To reversibly protect the most reactive amino groups in EPO (e.g., those amines associated with the Lys-52 side chain), the EPO solution was adjusted to pH 8.0 and then combined with a 10-fold molar excess of dimethylmaleic anhydride, "DMMAn", (Tsunoda, S., et al., *J. Pharmacol. Exp. Ther.* 1999, 290, 368-72) relative to the lysine amino acids in EPO, to thereby form a DMMAn-treated EPO solution. The pH was tested and adjusted as necessary to ensure a pH of 8.0.

Branched mPEG2-N-hydroxysuccinimide, 40 kDa, stored at −20° C. under argon, was warmed to ambient temperature. The branched mPEG2-N-hydroxysuccinimide, 40 kDa, (26.7 mg) was dissolved in 1.0 mL of 2 mM HCl to form a branched mPEG2-N-hydroxysuccinimide solution. The branched mPEG2-N-hydroxysuccinimide solution was added to the DMMAn-treated EPO solution (pH 8.0, room temperature), until a twenty-fold molar excess of branched mPEG2-N-hydroxysuccinimide relative to EPO was reached. To allow for coupling of the branched mPEG2-N-hydroxysuccinimide to EPO via an amide linkage, the reaction solution was stirred for two hours at room temperature and thereafter stirred for fourteen hours at 3-8° C. in a cold room, thereby resulting in a conjugate solution. The reaction was quenched by addition of glycine. Thereafter, to deprotect the protected lysine amino groups, the reaction mixture was adjusted to pH 6.0 with 0.1 N HCl and incubated at 37° C. for 30 minutes.

SDS-PAGE analysis was used for characterization. Based upon the SDS-PAGE results, the PEGylation yield of monoPEGylated conjugate (EPO 1-mer) was ~20%. It is believed that the DMMan preferentially reacted with the amino groups of Lys-52, thereby promoting conjugation of the mPEG-2-NHS reagent at sites other than Lys-52. The conjugate composition was purifed as previously described.

Based on RP-HPLC analysis, the purified monomer composition, designated herein as 01-P-MBNHS-40, contained 95+% monoPEGylatedEPO conjugate, and less than 5% diPEGylated EPO conjugate. The purified dimer composition, designated herein as 01-P-DBNHS-40, contained essentially pure diPEGylated EPO conjugate (RP-HPLC).

Based upon the reaction protocol used, it is believed that a majority of the conjugate species present in the resulting product mixture possess PEG covalently attached to a site other than the Lys-52, and that the resulting conjugates (and composition) retain higher bioactivity relative to PEG conjugates having attachment at Lys-52.

Using this same approach, other conjugates can be prepared using branched mPEG2-N-hydroxysuccinimide having other weight average molecular weights.

Example 8

Non-Random PEGylation of EPO with mPEG-SMB, 30 kDa

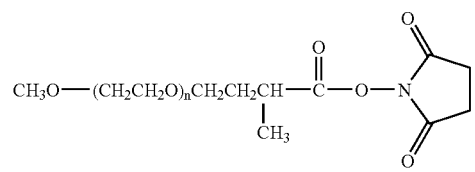

mPEG-SMB, 30 kDa

Prior to the conjugation reaction, 1.5 mL of reaction buffer (20 mM-200 mM NaPO$_4$) was added to 500 μL of stock EPO solution. To reversibly protect the most reactive amino groups in EPO (e.g., those amines associated with the Lys-52 side chain), the EPO solution was adjusted to pH 8.0 and was combined with a 10-fold molar excess of dimethylmaleic anhydride ("DMMAn") relative to the lysine amino acids in EPO, to thereby form a DMMAn-treated EPO solution. The pH was tested and adjusted as necessary to ensure a pH of 8.0.

mPEG-SMB, 30 kDa, stored at −20° C. under argon, was warmed to ambient temperature. The warmed mPEG-SMB, 30 kDa (30.0 mg) was dissolved in 1.0 mL of 2 mM HCl to form an mPEG-SMB solution. The mPEG-SMB solution was added to the DMMAn-treated EPO solution (pH 8.0, room temperature), until a thirty molar excess of mPEG-SMB relative to EPO was reached. To allow for coupling of the mPEG-SMB to EPO via an amide linkage, the reaction solution was stirred for five hours at room temperature and thereafter stirred for nineteen hours at 3-8° C. in a cold room, thereby resulting in a conjugate solution. The reaction was quenched by addition of a IM glycine solution. Thereafter, to deprotect the protected lysine amino groups, the reaction mixture was adjusted to pH 6.0 with 0.1 N HCl and incubated at 37° C. for 30 minutes.

SDS-PAGE was used for characterization. Based upon the SDS-PAGE results, the PEGylation yield of monoPEGylated conjugate (EPO 1-mer) was ~50%. Based upon the reaction protocol used, it is believed that a majority of the conjugate species present in the resulting product mixture possess PEG covalently attached to a site other than the Lys-52, and that the resulting conjugates (and composition) retain higher bioactivity relative to PEG conjugates having attachment at Lys-52. The product mixture was purified by ion exchange chromatography as previously described.

The purified monoPEGylated product, designated 01-P-MSMBE-30, was determined by RP-HPLC to contain approximately 91% monomer (mono-mPEG-SMB-30 kD-EPO) and 9% dimer (dimPEG-SMB-30 kD-EPO). No triP-EGylated product was detected. The purified di-PEGylated product, designated 01-P-DSMBE-30, was determined by RP-HPLC to contain approximately 94% dimer (di-mPEG-SMB-30 kD-EPO) and 6% monomer (mono-mPEG-SMB-30 kD-EPO). No triPEGylated product was detected.

Preliminary in vivo and in vitro assays were conducted on the conjugates, mono-mPEG-SMB-30 kD-EPO and di-mPEG-SMB-30 kD-EPO, as provided below. These results confirm the bioactivity of the subject conjugates.

TABLE 5

| Conjugate | In vivo Activity, IU/mg* | In vitro Assay** |
|---|---|---|
| mono-mPEG-SMB-30kD-EPO) Sample 01-P-MSMBE-30 | 203000 | 0.7% |
| di-mPEG-SMB-30kD-EPO Sample 01-P-DSMBE-30 | 77000 | 0.4% |

*unmodified EPO possesses an activity of 120,000 IU/mg in the assay set up employed.
**for comparison, unmodified EPO is considered to possess an activity of 100%.

Using this same approach, other conjugates can be prepared using mPEG-SMB having other weight average molecular weights.

Example 9

PEGylation of EPO with Branched mPEG-Butyraldehyde, 40 kDa

Branched mPEG2-Butyraldehyde, 40 kDa

PEGylation of EPO was carried out using a branched, N-terminus selective reagent as shown above.

Branched mPEG2-butyraldehyde, 40 kDa, stored at −20° C. under argon, was warmed to ambient temperature. The branched mPEG2-butyraldehyde (30.0 mg) was dissolved in 2.0 mL of 2 mM HCl to form a branched mPEG2-butyraldehyde solution. The branched mPEG2-butryaldehyde solution was added to a previously prepared EPO reaction mixture (500 μL stock EPO solution, 2 mL of 20 mM sodium acetate, pH 5.2) until a twenty molar excess of branched mPEG2-butryaldehyde to EPO was reached. After addition of the branched mPEG2-butryaldehyde, the pH was tested and adjusted as necessary to ensure a pH of about 6.5. A reducing agent, $NaCNBH_3$, was added at a ten-fold molar excess relative to the branched mPEG2-butyraldehyde (with the pH tested and adjusted as necessary to ensure a pH of about 6.5). The solution was then stirred for 24 hours at 4° C. to ensure coupling via an amine linkage.

The product mixture was analyzed by SDS-PAGE. Based upon the SDS-PAGE results, the PEGylation yield of the monoPEGylated conjugate (EPO 1-mer) formed by reaction of EPO with branched mPEG2-butyraldehyde was ~50%. It is believed that the mixture contained fewer than 50% EPO-conjugate species having PEG attached at Lys-52, and fewer than 50% EPO-conjugate species having PEG attached at the N-terminal. SDS-PAGE analysis of the purified product, designated as 01-N-MBC4ALDE-40, demonstrated formation of essentially all, i.e., 100%, monoPEGylated EPO.

The product mixture was purified by ion exchange chromatography as previously described. The standard chromatogram of the purified conjugate product confirmed production of primarily mono-PEGylated product (~80%), although a small amount of dimer (~20%) was detected using this technique. SDS-PAGE analysis also indicated that the sample contained only minimal amounts of higher-PEGylated by-product(s), and confirmed the near homogeneity of the preparation. MALDI-TOF was used to determine molecular mass; 01-N-MBC4ALDE-40 was determined to have a molecular mass of approximately 72 kDa, thereby confirming mono-PEGylation of EPO with the branched mPEG2-butyraldehyde 40 kD reagent.

Using this same approach, other conjugates can be prepared using branched mPEG2-butyraldehyde having other weight average molecular weights.

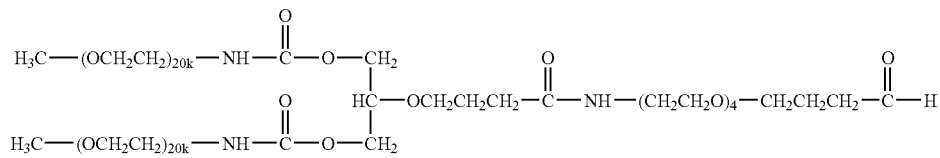

Example 10

PEGylation of EPO with Branched mPEG-Butyraldehyde, 40 kDa

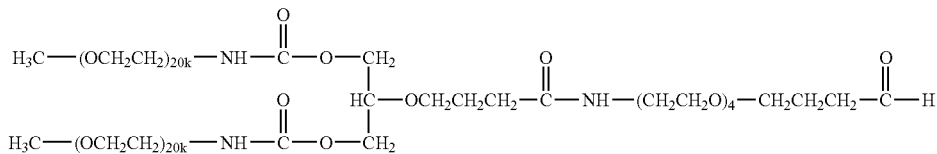

Branched mPEG2-Butyraldehyde, 40 kDa

PEGylation of EPO was carried out using a branched, N-terminus selective reagent as shown above under slightly different reaction conditions from those employed in the preceding example.

Branched mPEG2-butyraldehyde, 40 kDa, stored at −20° C. under argon, was warmed to ambient temperature. The branched mPEG2-butyraldehyde (30.0 mg) was dissolved in 2.0 mL of 2 mM HCl to form a branched mPEG2-butyraldehyde solution. The branched mPEG2-butryaldehyde solution was added to a previously prepared EPO reaction mixture (500 μL stock EPO solution, 2 mL of 20 mM sodium acetate, pH 5.2) until a ten-fold molar excess of branched mPEG2-butyraldehyde to EPO was reached. After addition of the branched mPEG2-butyraldehyde, the pH was tested and adjusted as necessary to ensure a pH of about 6.5. A reducing agent, NaCNBH$_3$, was added at a five-fold molar excess relative to the branched mPEG2-butyraldehyde (with the pH tested and adjusted as necessary to ensure a pH of about 6.5). After one hour, another ten-fold molar excess of branched mPEG2-butyraldehyde to EPO was added. Again, the pH was tested and adjusted as necessary to ensure a pH of about 6.5. A second reducing step was performed by adding NaCNBH$_3$ at a five-fold molar excess relative to the second amount of branched mPEG-2 butyraldehdye added to the solution (with the pH tested and adjusted as necessary to ensure a pH of about 6.5). The solution was then stirred for 24 hours at 4° C. to ensure coupling via an amine linkage, thereby resulting in a conjugate solution.

The conjugate solution was purified using ion exchange chromatography (anion-strong). SDS-PAGE and RP-HPLC (C$_3$) analysis were also used for the characterization. Based upon the purification and analysis, the PEGylation yield of monoPEGylated conjugate (EPO 1-mer) was ~35%.

The composition is expected to comprise a mixture of monoPEGylated isoforms having polymer attachment the N-terminal, Lys-52, and other amines.

Using this same approach, other conjugates can be prepared using branched mPEG2-butyraldehyde having other weight average molecular weights.

Example 11

PEGylation of EPO with mPEG-SPA, 20 kDa mPEG-Succinimidyl propionate having a molecular weight of 20,000 Daltons is obtained from Nektar Therapeutics, (Huntsville, Ala.). The basic structure of the PEG reagent is provided below:

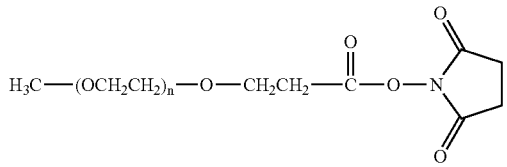

mPEG-SPA, 20 kDa

To a buffered solution of EPO is added base, e.g., NaOH or an acid equivalent such as HCl, to adjust the pH to approximately 5.5-8.5. To the above solution is added a 1.5 to 10-fold molar excess of the PEG reagent, mPEG-SPA, 20 kDa. The resulting mixture is stirred at room temperature for several hours. Analysis of the reaction mixture reveals successful conjugation of EPO.

Using this same approach, other conjugates can be prepared using mPEG-SPA having other weight average molecular weights.

Example 12

PEGylation of EPO with mPEG-SMP, 10 kDa mPEG-SMP having a molecular weight of 10,000 Daltons is obtained from Nektar Therapeutics, (Huntsville, Ala.). The basic structure of the PEG reagent is provided below:

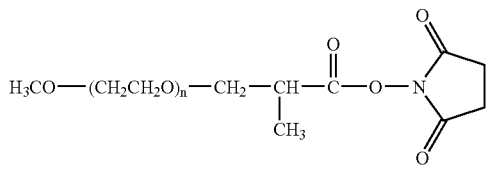

mPEG-SMP, 10 kDa

To an aqueous solution of EPO is added a base such as NaOH or an acid equivalent such as HCl to adjust the pH to approximately 5.5-8.5. To this solution is then added a 1.5 to 10-fold molar excess of PEG reagent, mPEG-SMP, 10 kDa. The resulting mixture is stirred at room temperature for several hours. Analysis of the reaction mixture reveals successful conjugation of EPO.

Using this same approach, other conjugates can be prepared using mPEG-SMP having other weight average molecular weights.

Example 13

PEGylation of Engineered EPO with mPEG-MAL, 20 kDa mPEG-Maleimide having a molecular weight of 20,000 Daltons is obtained from Nektar Therapeutics, (Huntsville, Ala.). The basic structure of the polymeric reagent is provided below:

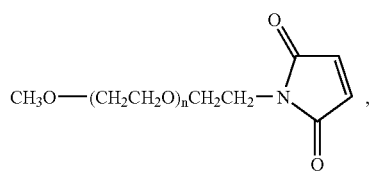

mPEG-MAL, 20 kDa

EPO engineered to include a cysteine residue (see, e.g., Cox et al., U.S. Pat. No. 6,753,165, or Shaw, et al., WO 90/12874) is stored in buffer. To this protein solution is added a 3-5 fold molar excess of mPEG-MAL, 20 kDa. The mixture is stirred at room temperature under an inert atmosphere for several hours. Analysis of the reaction mixture reveals successful conjugation of EPO.

Using this same approach, other conjugates can be prepared using mPEG-MAL having other weight average molecular weights.

Example 14

PEGylation of Engineered EPO with mPEG-OPSS, 20 kDa mPEG-OPSS having a molecular weight of 20,000 Daltons is obtained from Nektar Therapeutics, (Huntsville, Ala.). The basic structure of the polymeric reagent is provided below:

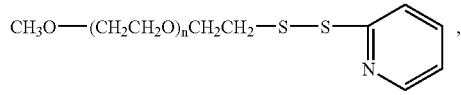

mPEG-OPSS, 20 kDa

EPO engineered to include a cysteine residue is stored in buffer. To this protein solution is added a 3-5 fold molar excess of mPEG-OPSS, 20 kDa. The mixture is stirred at room temperature under an inert atmosphere for several hours. Analysis of the reaction mixture reveals successful conjugation of EPO.

Using this same approach, other conjugates can be prepared using mPEG-OPSS having other weight average molecular weights.

Example 15

PEGylation of EPO with mPEG-PIP, 5 kDa mPEG-PIP having a molecular weight of 5,000 Daltons is obtained from Nektar Therapeutics, (Huntsville, Ala.). The basic structure of the polymeric reagent is provided below:

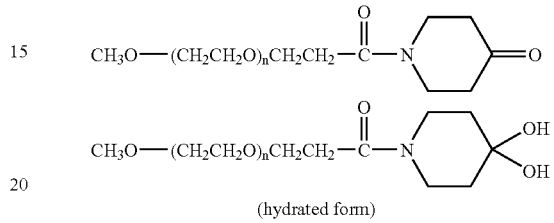

(hydrated form)

A 20-fold molar excess of PEG reagent, mPEG-PIP, 5 kDa, is added to a buffered solution of EPO. The resulting solution is placed on an orbital shaker set at slow speed to facilitate reaction at room temperature. After 15 minutes, aqueous NaCNBH$_3$ is added in an amount equal to a 50 fold-molar excess relative to EPO. Aliquots are withdrawn at timed intervals from the reaction mixture and are analyzed to determine the rate of conjugation. After 24 hours, analysis of the reaction mixture reveals successful conjugation of EPO.

Using this same approach, other conjugates can be prepared using mPEG-PIP having other weight average molecular weights.

Example 16

In-vitro Activity of Exemplary PEG-EPO Conjugates

The in-vitro activities of the PEG-EPO conjugates described in the preceding Examples are determined, e.g., by measuring dose dependent proliferation activities using EPO-responsive target cells, e.g., primary murine spleen cells (Krystal, G., (1983), *Exp. Hematol.,* 11, 649-60), HCD 57, a murine MEL cell line developed by Hankins et al., (1987), *Blood,* 70, 173a), and/or UT7-EPO, a human cell line derived from the bone marrow of a patient with acute megakaryoblastic leukemia (Komatsu, N., et al., (1991), *Cancer Res* 51, 341-348).

All of the EPO conjugates described herein for which bioactivity data is not specifically included are believed to be bioactive.

Example 17

In-vitro Activity of Certain Exemplary PEG-EPO Conjugates

The biologic activity of the EPO conjugates from Example 3 and Example 9 was assessed using a normocythaemic mouse assay (European Pharmacopoia 2002). Test dilutions were based on sample concentrations as provided below and a rough estimation of a specific potency of 360 kIU/mg. The concentrations were determined using the Bradford method (Bradford, M. M., ibid, 1976) or by RP-HPLC by creating a standard curve using either BSA (bovine serum albumin) or EPO as the standard.

TABLE 6

Sample Concentrations

| Sample Description | Designation | Example Cross Reference | Concentration | Total Volume |
|---|---|---|---|---|
| Native EPO | NR | NR | 2.1 mg/ml | 1 ml |
| Native control EPO | NR | NR | 0.29 mg/ml | 9 ml |
| Mono-mPEG-SMB-30kD-EPO | 01-R-MSMBE-30 | Example 3 | 0.19 mg/ml | 17.4 ml |
| Di-mPEG-SMB-30kD-EPO | 01-R-DSMBE-30 | Example 3 | 0.17 mg/ml | 14 ml |
| Mono-branched mPEG2-4-amino-butylene-NH-EPO (from branched mPEG-2 butyr-aldehyde reagent) | 01-N-MBC4ALDE-40 | Example 9 | 0.203 mg/ml | 12.5 ml |
| Native Control EPO | NR | NR | 0.572 mg/ml | 10 ml |

The following reported biological activities represent an approximate determination due to a degree of uncertainty regarding the true content of the PEGylated samples. A first attempt to measure the samples using test statistics failed based on a validity level of p>0.95. The data was recalculated using p>0.90 and are summarized below.

The assays indicated an increase in biological activity for both the two monoPEGylated EPO compositions, 01-R-MSMBE-30, and 01-N-MBC4ALDE-40, as well as the diP-EGylated composition, 01-R-DSMBE-30. The observed increase in biologic activity was similar for each of the samples tested. The calculated biologic activity was 276 kIU/mg for 01-R-MSMBE-30, 256 kIU/mg for 01-R-DSMBE-30, and 316 kIU/mg for 01-N-MBC4ALDE-40-approximately 2.1 to 2.6 times higher than that of the EPO reference material.

These results demonstrate that PEGylation of EPO to produce EPO conjugates having one or two molecules of these exemplary PEGs covalently attached to EPO results in EPO conjugates having demonstrated biologic activity.

Example 18

Peptide Mapping of PEG-EPO Conjugates

Peptide mapping was carried out for EPO and various PEG-EPO conjugates, 01-R-MSMBE-30 (Example 3), 01-R-DSMBE-30 (Example 3), and 01-N-MBC4ALDE-40 (Example 9). Each of the samples was digested with trypsin, separated by reverse phase chromatography, detected by UV-absorbance, and analyzed by electrospray ionization mass spectrometric detection.

FIGS. 1A-D provide total ion current spectra of EPO and the PEG-EPO conjugates described above. The T6-fragment VNFYAWK (SEQ ID NO: 3) and the T6+T7 fragment VNFYAWKR (SEQ ID NO: 4) contained the lysine at position 52. The digests of all PEGylated conjugates contained minor or no signals at the retention time corresponding to the tryptic fragments T6+T7 (51 minutes) and T6 (63.6 minutes). Due to incomplete digests, a preliminary conclusion regarding the distribution of species in the samples and their respective sites of PEGylation was not reached.

Additional peptide mapping studies were carried out on the conjugates described in Example 8. Preliminary results are summarized in the table below.

TABLE 7

| Protein Site | 01-P-MSMBE-30 (Example 8, Monomer) % PEGylated | 01-P-DSMBE-30 (Example 8, Dimer) % PEGylated |
|---|---|---|
| Lys 45/52 | ~45 | ~60 |
| N-terminal | ~20 | ~50 |
| Lys 97/116 | ~35 | ~55 |
| Lys 20/140/153/155 | n.a. | n.a. |

Example 19

Pharmacokinetic Study in Rats

The mono-mPEG-SMB-30 kD-EPO conjugate described in Example 8, 01-P-MSMBE-30, was evaluated in a pharmacokinetic study in rats. The in vivo bioactivity of the conjugate was determined to be approximately 500,000 IU/mg, while its in vitro activity was assessed in preliminary assays as 1.9%.

Figure 2:
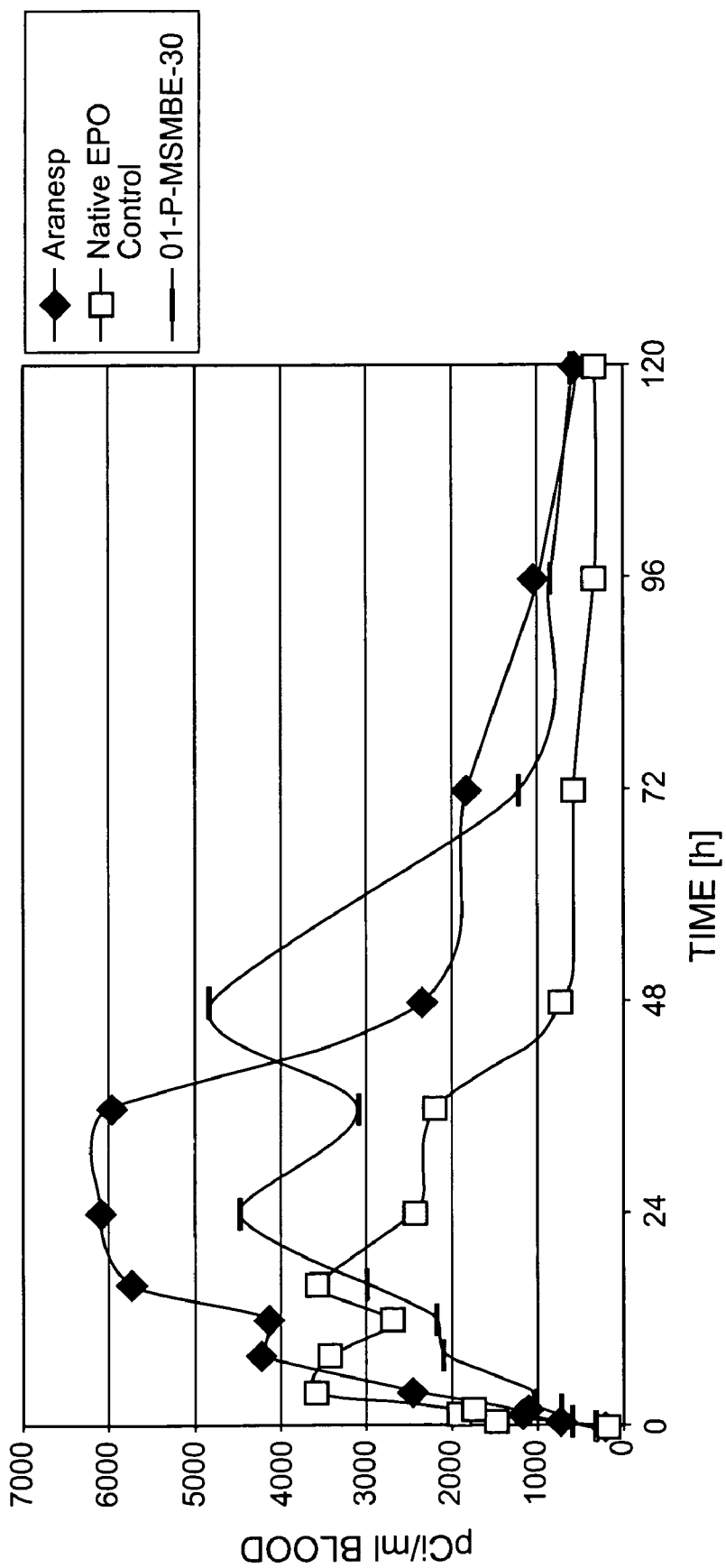
FIG. 2 is a plot demonstrating the comparative blood levels over time for unmodified EPO, Aranesp®, and an exemplary EPO conjugate in accordance with the invention, 01-P-MSMBE-30, when subcutaneously administered to mice as described in Example 19.

Native EPO (used as a control), a marketed version of an erythropoiesis-stimulating protein closely related to EPO, Aranesp®, and mono-mPEG-SMB-30 kD-EPO, were used in the comparative study. Proteins were radiolabeled with $^{125}$I using the chloramin-T method (Ilondo M M, et al., *Biochem Biophys Res Commun*, 1986, 134:671-677). Mice were dosed subcutaneously at 4 µCi/kg body weight. Dosing was conducted on five subgroups of four mice each. Blood samples were taken at various time points as indicated and analyzed. The results are shown in FIG. 2.

As can be seen, the mono-mPEG-SMB-30 kD-EPO conjugate sustains higher blood levels over an extended period of time than either the native EPO control or the marketed product, Aranesp®. Thus, this exemplary conjugate exhibits a distinctly different pharmacokinetic profile then either native EPO or Aranesp®, and also possesses a notable advantage over each by virtue of its higher and sustained blood levels over time.

The invention claimed is:

1. A conjugate of erythropoietin (EPO) having the structure:

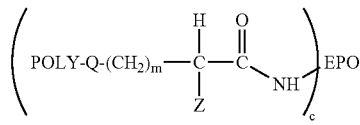

wherein:
POLY is a polyalkylene oxide,
Q is an optional linking group having a length of from one to 10 atoms,
m is an integer ranging from 0 to 20,
Z is selected from the group consisting of alkyl, substituted alkyl, aryl and substituted aryl,
c is an integer from 1 to 5
EPO is a residue of erythropoietin, and
"—NH-EPO" represents an amino group of EPO, wherein said EPO corresponds to SEQ ID NO: 1 or SEQ ID NO: 2.

2. The conjugate of claim 1, wherein POLY is a polyethylene glycol (PEG).

3. The conjugate of claim 2, wherein Q has a length of from one to five atoms.

4. The conjugate of claim 1, wherein Q is absent.

5. The conjugate of claim 1, wherein m is an integer selected from the group consisting of 0, 1, 2, 3, 4, 5, 6, 7, 8, 9, and 10.

6. The conjugate of claim 5, wherein m is 2 or 3.

7. The conjugate of claim 1, wherein Z is lower alkyl or substituted lower alkyl.

8. The conjugate of claim 5, wherein Z is selected from the group consisting of methyl, ethyl, n-propyl, isopropyl, n-butyl, and isobutyl.

9. The conjugate of claim 8, wherein Z is methyl.

10. The conjugate of claim 2, wherein said PEG is linear or branched.

11. The conjugate of claim 2, wherein said POLY possesses a weight average molecular weight from about 10,000 Daltons to about 60,000 Daltons.

12. The conjugate of claim 11, wherein said POLY possesses a weight average molecular weight selected from the group consisting of about 20 kilodaltons, about 30 kilodaltons, about 40 kilodaltons, and about 50 kilodaltons.

13. The conjugate of claim 12, wherein said POLY possesses a weight average molecular weight of about 30 kilodaltons.

14. The conjugate of claim 1, comprising the structure:

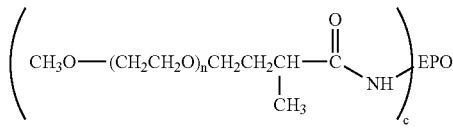

wherein n ranges from about 200 to about 1400.

15. The conjugate of claim 14, wherein said EPO corresponds to SEQ ID NO:1 or SEQ ID NO:2.

16. The conjugate of claim 14, wherein said conjugate is a monoPEGylated EPO conjugate.

17. The conjugate of claim 14, wherein said conjugate is a diPEGylated EPO conjugate.

18. A composition comprising the conjugate of claim 14, wherein greater than about 85% of said PEG-EPO conjugates in the composition are monoPEGylated EPO.

19. The composition of claim 18, wherein greater than about 90% of the PEG-EPO conjugates in said composition are monoPEGylated EPO.

20. A composition comprising the conjugate of claim 16, wherein a minority of EPO conjugate species comprised in said composition have PEG covalently attached at lysine 52.

21. The composition of claim 16, comprising a combination of monoPEGylated EPO and diPEGylated EPO.

22. The composition of claim 20, comprising a minority of EPO conjugate species have PEG covalently attached at the N-terminus.

23. A pharmaceutical composition comprising the conjugate of claim 1 and a pharmaceutically acceptable excipient.

24. A pharmaceutical composition comprising the conjugate of claim 14 and a pharmaceutically acceptable excipient.

* * * * *

UNITED STATES PATENT AND TRADEMARK OFFICE
CERTIFICATE OF CORRECTION

Page 1 of 1

| | |
|---|---|
| PATENT NO. | : 7,714,114 B2 |
| APPLICATION NO. | : 11/357936 |
| DATED | : May 11, 2010 |
| INVENTOR(S) | : Mary J. Bossard et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 845 days.

Signed and Sealed this
Twenty-second Day of February, 2011

David J. Kappos
*Director of the United States Patent and Trademark Office*